US012662486B2

(12) United States Patent
Muthusamy et al.

(10) Patent No.: US 12,662,486 B2
(45) Date of Patent: Jun. 23, 2026

(54) SOLID STATE FORMS OF AT-001 AND PROCESS FOR PREPARATION THEREOF

(71) Applicant: ASSIA CHEMICAL INDUSTRIES LTD., Tel Aviv (IL)

(72) Inventors: Anantha Rajmohan Muthusamy, Sivakasi (IN); Amit Singh, Greater Noida (IN); Yogesh Dhananjay Wagh, Badlapur (IN)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 574 days.

(21) Appl. No.: 18/020,297

(22) PCT Filed: Sep. 7, 2021

(86) PCT No.: PCT/US2021/049201
§ 371 (c)(1),
(2) Date: Feb. 8, 2023

(87) PCT Pub. No.: WO2022/055836
PCT Pub. Date: Mar. 17, 2022

(65) Prior Publication Data

US 2023/0322786 A1 Oct. 12, 2023

(30) Foreign Application Priority Data

Sep. 8, 2020 (IN) ............................. 202011038787
Oct. 6, 2020 (IN) ............................. 202011043485
Aug. 3, 2021 (IN) ............................. 202111034984

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC .......................... C07D 487/04; C07B 2200/13
USPC .......................................................... 514/249
See application file for complete search history.

(56) References Cited

U.S. PATENT DOCUMENTS 6,159,976 A * 12/2000 Lambert .................. A61P 3/06
544/239
10,640,487 B2 * 5/2020 Ceric ...................... A61P 35/00

FOREIGN PATENT DOCUMENTS

| | | | | | |
|---|---|---|---|---|---|
| AU | 2021106179 | A4 * | 10/2021 | ............. | C07B 37/04 |
| EP | 2593456 | B1 | 11/2016 | | |
| WO | WO-2012009553 | A1 * | 1/2012 | ........... | C07D 487/04 |
| WO | WO-2017160703 | A1 * | 9/2017 | ........... | C07D 401/14 |

OTHER PUBLICATIONS

NCT04083339 V2, 2019, Safety and Efficacy of AT-001 in Patients With Diabetic Cardiomyopathy, retrieved from https://clinicaltrials.gov/study/NCT04083339 (Year: 2019).*
International Search Report and Written Opinion of the International Searching Authority issued in corresponding application PCT/US2021/049201 mailed Nov. 11, 2021 (9 pages).

* cited by examiner

*Primary Examiner* — Jared Barsky
*Assistant Examiner* — Liyuan Mou
(74) *Attorney, Agent, or Firm* — Carter, DeLuca & Farrell, LLP

(57) ABSTRACT

The present disclosure encompasses solid state forms of AT-001, in embodiments crystalline polymorphs of AT-001 or salts or co-crystals of AT-001, processes for preparation thereof, and pharmaceutical compositions thereof.

6 Claims, 21 Drawing Sheets

X-Ray Powder Diffraction Pattern of crystalline AT-001: Isonicotinamide (Form AC2)

X-Ray Powder Diffraction Pattern of crystalline AT-001: Nicotinamide (Form AC3)

X-Ray Powder Diffraction Pattern of AT-001 Form J $^{13}C$ solid state NMR spectrum of Form B of AT-001 (full scan)

$^{13}C$ solid state NMR spectrum of Form A of AT-001 (at the range of 0-100 ppm)

$^{13}C$ solid state NMR spectrum of Form A of AT-001 (at the range of 100-200 ppm)

SOLID STATE FORMS OF AT-001 AND PROCESS FOR PREPARATION THEREOF

CROSS REFERENCE TO RELATED APPLICATIONS

This application is a National Stage of, and claims priority to and the benefit of, International Patent Application No. PCT/US2021/049201, filed Sep. 7, 2021, which, in turn, claims the benefit of and priority to, Indian Provisional Application No. 202011038787, filed Sep. 8, 2020; Indian Provisional Application No. 202011043485, filed Oct. 6, 2020; and Indian Provisional Application No. 202111034984, filed Aug. 3, 2021, the entire disclosures of each of which are incorporated by reference herein.

FIELD OF THE DISCLOSURE

The present disclosure encompasses solid state forms of AT-001, in embodiments crystalline polymorphs of AT-001 or salts or co-crystals of AT-001, processes for preparation thereof, and pharmaceutical compositions thereof.

BACKGROUND OF THE DISCLOSURE

AT-001, 2-(8-oxo-7-((5-(trifluoromethyl)benzo[d]thiazol-2-yl)methyl)-7,8-dihydropyrazino[2,3-d]pyridazin-5-yl) acetic acid, has the following chemical structure:

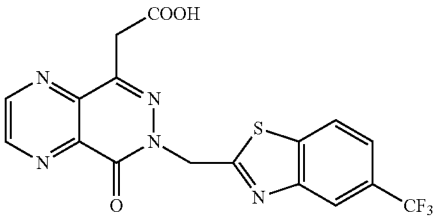 [SMILES: O=C(O)Cc1nn(Cc2nc3cc(C(F)(F)F)ccc3s2)c(=O)c2nccnc12]

AT-001 is an Aldose Reductase inhibitor and it is developed for the treatment of Diabetic Cardiomyopathy. AT-001 is also under investigation as a potential treatment for: Diabetic Peripheral Neuropathy, acute lung inflammation and cardiomyopathy in critical COVID-19 patients.

The compound is described in International Publication No. WO 2012/009553.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of AT-001.

SUMMARY OF THE DISCLOSURE

The present disclosure provides crystalline polymorphs of AT-001, or salts or co-crystals, processes for preparation thereof, and pharmaceutical compositions thereof. These crystalline polymorphs can be used to prepare other solid state forms of AT-001, AT-001 salts or co-crystals and their solid state forms.

In embodiments, the present disclosure provides AT-001 and crystalline forms thereof. In embodiments, the present disclosure provides crystalline form of AT-001 designated as Form A, Form B, Form C, Form D, Form E, Form F, Form G, Form H, Form I, Form J, Form K, Form AC1, Form AC2 and/or Form AC3 (defined herein).

The present disclosure also provides uses of the said solid state forms of AT-001 in the preparation of other solid state forms of AT-001 or salts or co-crystals thereof.

The present disclosure provides crystalline polymorphs of AT-001 for use in medicine, including for the treatment of Diabetic Cardiomyopathy, Diabetic Peripheral Neuropathy, acute lung inflammation in critical COVID-19 patients, or cardiomyopathy in critical COVID-19 patients, and preferably Diabetic Cardiomyopathy.

The present disclosure also encompasses the use of crystalline polymorphs of AT-001 of the present disclosure for the preparation of pharmaceutical compositions and/or formulations.

In another aspect, the present disclosure provides pharmaceutical compositions comprising crystalline polymorphs of AT-001 according to the present disclosure.

The present disclosure includes processes for preparing the above mentioned pharmaceutical compositions. The processes include combining any one or a combination of the crystalline polymorphs of AT-001 with at least one pharmaceutically acceptable excipient.

The crystalline polymorph of AT-001 as defined herein and the pharmaceutical compositions or formulations of the crystalline polymorph of AT-001 may be used as medicaments, such as for the treatment of Diabetic Cardiomyopathy, Diabetic Peripheral Neuropathy, acute lung inflammation in critical COVID-19 patients, or cardiomyopathy in critical COVID-19 patients, and preferably Diabetic Cardiomyopathy.

The present disclosure also provides methods of treating Diabetic Cardiomyopathy, Diabetic Peripheral Neuropathy, acute lung inflammation in critical COVID-19 patients, or cardiomyopathy in critical COVID-19 patients, and preferably Diabetic Cardiomyopathy, by administering a therapeutically effective amount of any one or a combination of the crystalline polymorphs of AT-001 of the present disclosure, or at least one of the above pharmaceutical compositions, to a subject suffering from Diabetic Cardiomyopathy, Diabetic Peripheral Neuropathy, acute lung inflammation in critical COVID-19 patients, or cardiomyopathy in critical COVID-19 patients, or preferably Diabetic Cardiomyopathy, or otherwise in need of the treatment.

The present disclosure also provides uses of crystalline polymorphs of AT-001 of the present disclosure, or at least one of the above pharmaceutical compositions, for the manufacture of medicaments for treating e.g., Diabetic Cardiomyopathy, Diabetic Peripheral Neuropathy, acute lung inflammation in critical COVID-19 patients, or cardiomyopathy in critical COVID-19 patients, and preferably Diabetic Cardiomyopathy.

DETAILED DESCRIPTION OF THE DISCLOSURE

Figure 1:
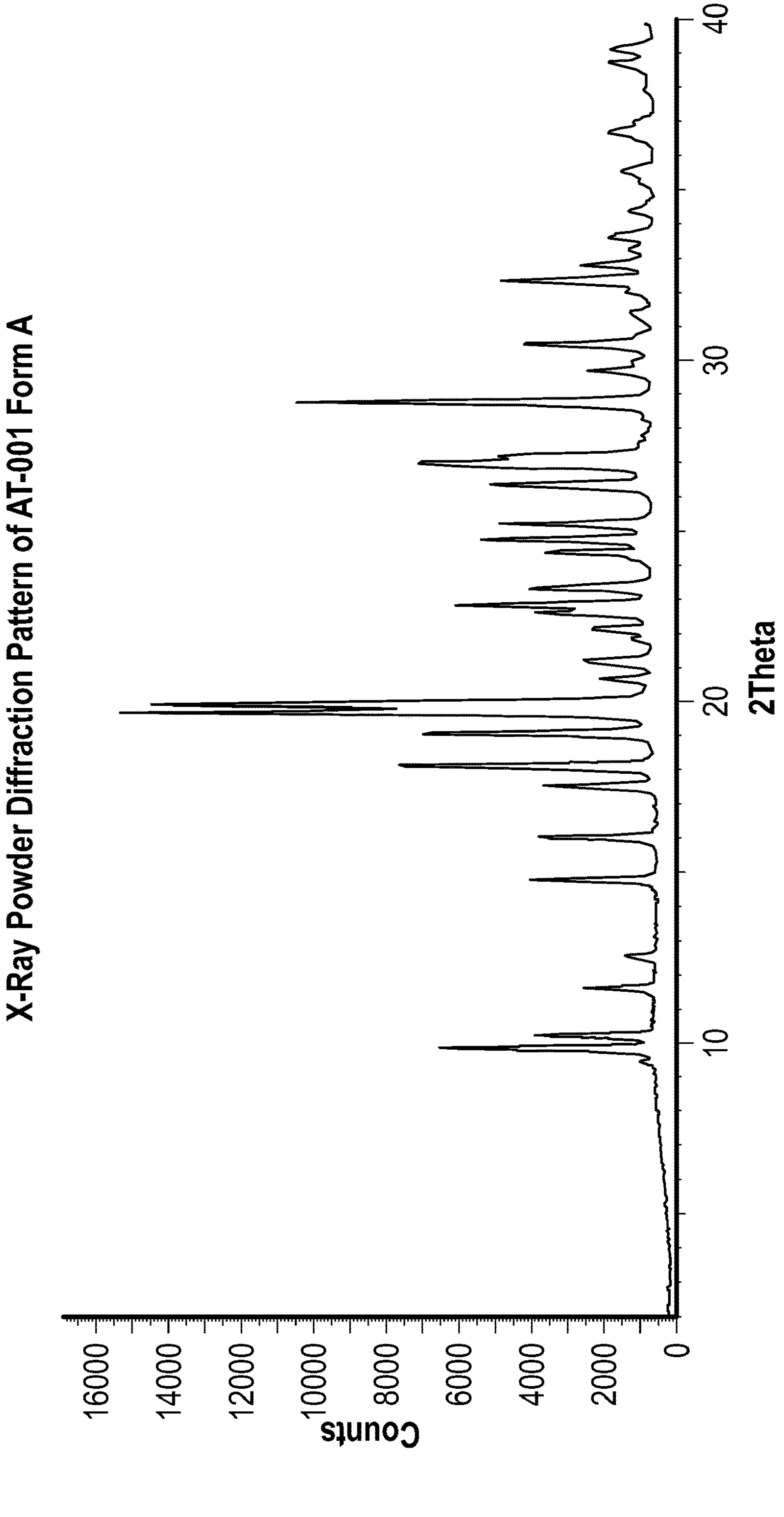
FIG. 1 shows a characteristic X-ray powder diffraction pattern (XRPD) of AT-001 Form A.

The present disclosure encompasses solid state forms of AT-001, including crystalline polymorphs of AT-001, processes for preparation thereof, and pharmaceutical compositions thereof.

In embodiments, the present disclosure provides AT-001 and crystalline forms thereof. In embodiments, the present disclosure provides crystalline form of AT-001 designated as Form A, Form B, Form C, Form D, Form E, Form F, Form G, Form H, Form I, Form J, Form K, Form AC1, Form AC2 and/or Form AC3 (defined herein).

Solid state properties of AT-001 and crystalline polymorphs thereof can be influenced by controlling the conditions under which AT-001 and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of AT-001 described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of AT-001. In some embodiments of the disclosure, the described crystalline polymorph of AT-001 may contain from about 1% to about 20% (w/w), from about 5% to about 20% (w/w), or from about 5% to about 10% (w/w) of one or more other crystalline polymorph of the same AT-001.

Depending on which other crystalline polymorphs a comparison is made, the crystalline polymorphs of AT-001 of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, in flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of AT-001 referred to herein as being characterized by graphical data "as depicted in" or "as substantially depicted in" a Figure will thus be understood to include any crystal forms of AT-001 characterized with the graphical data having such small variations, as are well known to the skilled person, in comparison with the Figure.

As used herein, and unless stated otherwise, the term "anhydrous" in relation to crystalline forms of AT-001, relates to a crystalline form of AT-001 which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

"Co-Crystal" or "Co-crystal" as used herein is defined as a crystalline material including two or more molecules in the same crystalline lattice and associated by non-ionic and non-covalent bonds. In some embodiments, the co-crystal includes two molecules which are in natural state.

As used herein, the term "isolated" in reference to crystalline polymorph of AT-001 of the present disclosure corresponds to a crystalline polymorph of AT-001 that is physically separated from the reaction mixture in which it is formed.

As used herein, unless stated otherwise, the XRPD measurements are taken using copper Kα radiation wavelength 1.5418 Å. XRPD peaks reported herein are measured using Cuk α radiation, λ=1.5418 Å, typically at a temperature of 25±3° C.

As used herein, unless stated otherwise, $^{13}C$ NMR reported herein are measured at 125 MHz at a magic angle spinning frequency $\omega_r/2\pi$=11 kHz, preferably at a temperature of at 293 K±3° C.

As used herein, unless stated otherwise, differential scanning calorimetry (DSC) measurements are measured under nitrogen at a heating rate of 1° C./min up to 250° C.

As used herein, unless stated otherwise, thermogravimetric analysis (TGA) is measured under nitrogen at a heating rate of 10° C./min up to 350° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

Figure 17A:
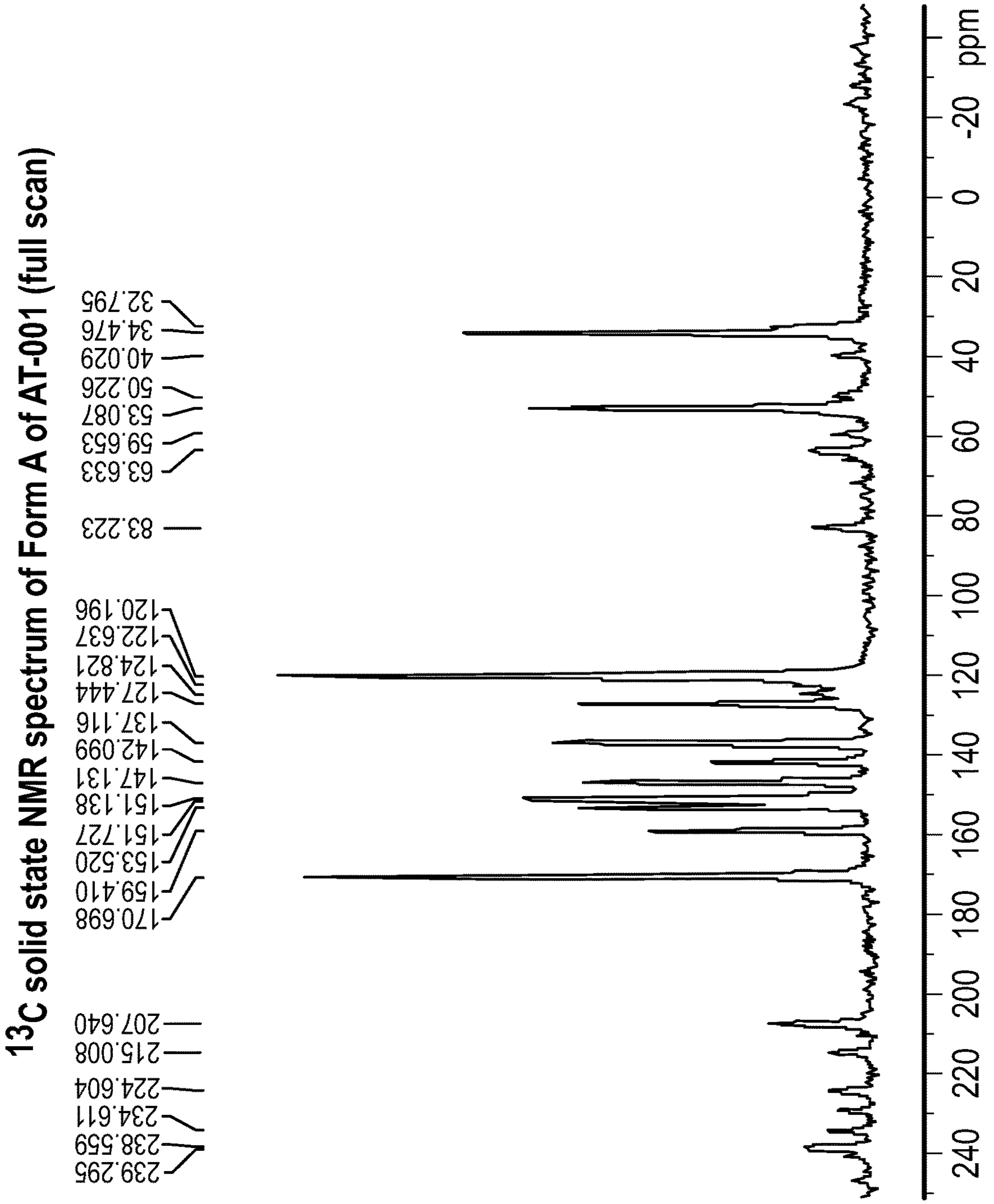
FIG. 17*a* shows $^{13}C$ solid state NMR spectrum of Form A of AT-001 (full scan).
Figure 17B:
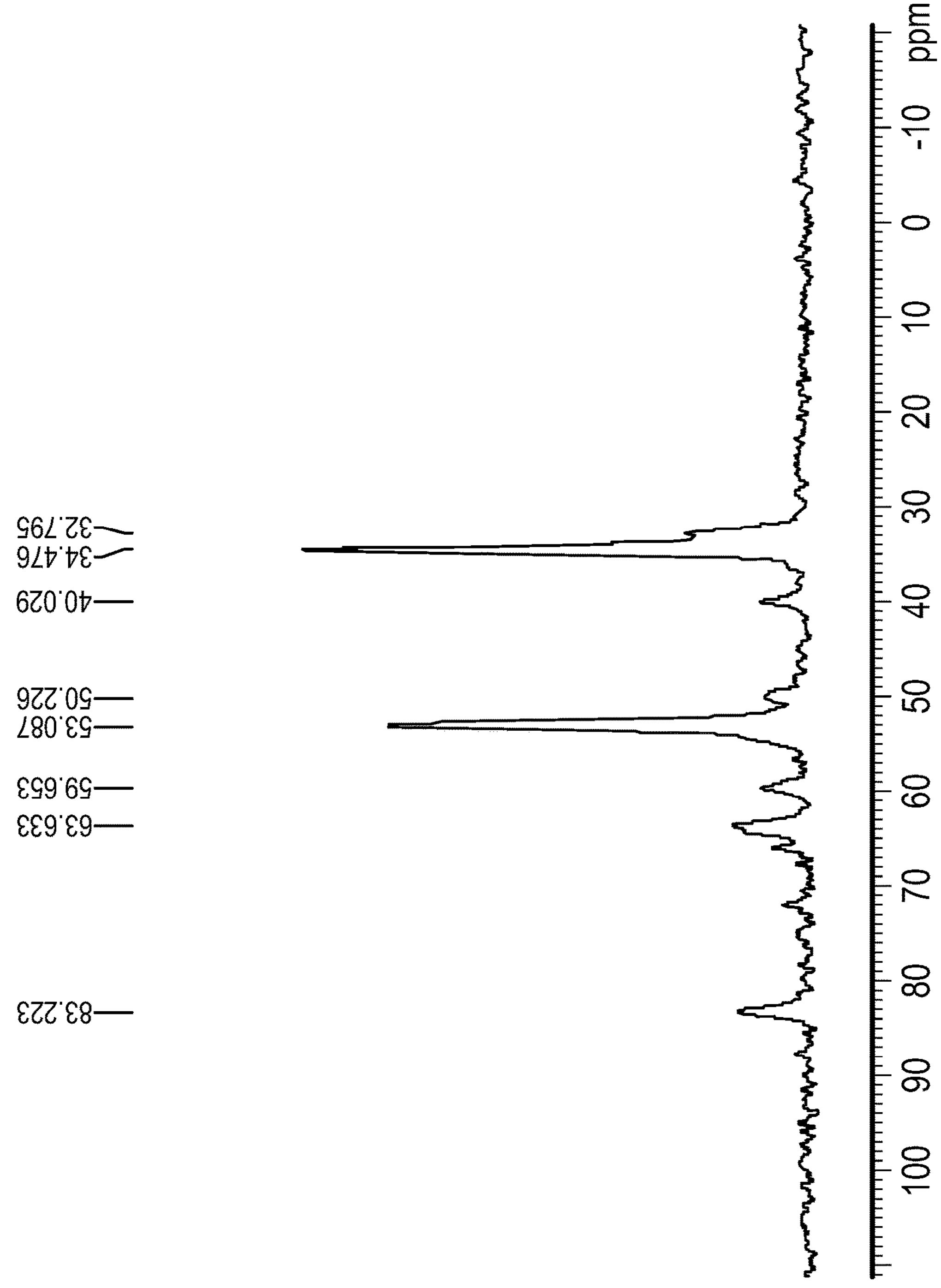
FIG. 17*b* shows $^{13}C$ solid state NMR spectrum of Form A of AT-001 (at the range of 0-100 ppm).
Figure 17C:
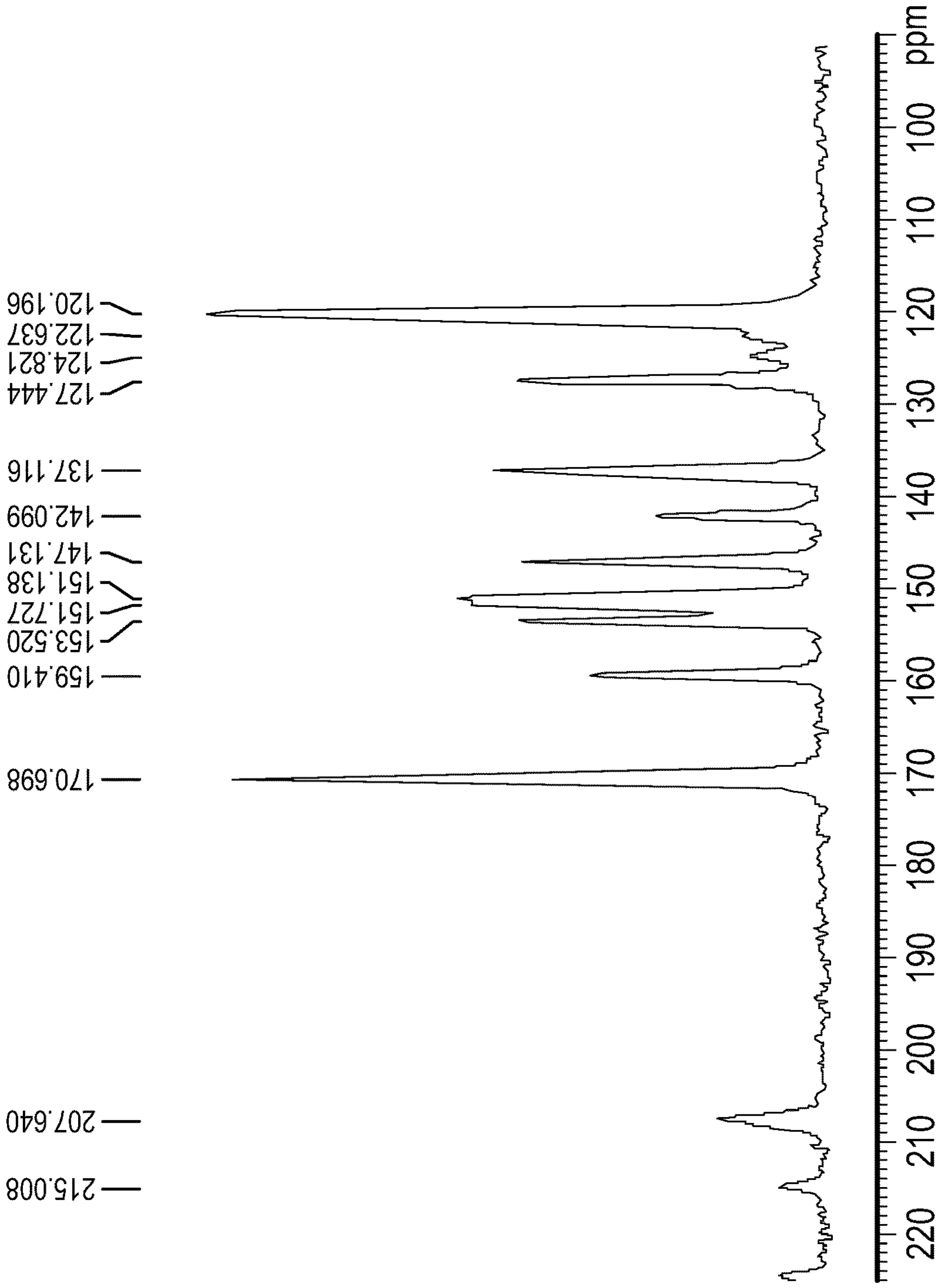
FIG. 17*c* shows $^{13}C$ solid state NMR spectrum of Form A of AT-001 (at the range of 100-200 ppm).

The present disclosure includes a crystalline polymorph of AT-001, designated Form A. The crystalline Form A of AT-001 may be characterized by data selected from one or more of the following: an X-ray powder diffraction pattern substantially as depicted in FIG. 1; an X-ray powder diffraction pattern having peaks at 9.8, 19.0, 19.9, 25.2 and 28.8 degrees 2-theta±0.2 degrees 2-theta; a solid state $^{13}C$ NMR spectrum having peaks at 53.1, 122.6, 147.1, 151.1, 153.5 and 170.7 ppm±0.2 ppm; a solid state $^{13}C$ NMR spectrum having the following chemical shift absolute differences from a reference peak at 34.5 ppm±2 ppm of 18.6, 88.1, 112.6, 116.6, 119.0 and 136.2 ppm±0.1 ppm; a solid state $^{13}C$ NMR spectrum substantially as depicted in FIG. 17*a*, 17*b* or 17*c*; and combinations of these data; and combinations of these data.

Crystalline Form A of AT-001 may be further characterized by an X-ray powder diffraction pattern having peaks at 9.8, 19.0, 19.9, 25.2 and 28.8 degrees 2-theta±0.2 degrees 2-theta, and also having any one, two, three, or four additional peaks selected from 18.1, 21.2, 22.8 and 23.3 degrees 2-theta±0.2 degrees 2-theta.

Crystalline Form A of AT-001 may be alternatively characterized by an X-ray powder diffraction pattern having peaks at 9.8, 18.1, 19.0, 19.9, 21.2, 22.8, 23.3, 25.2 and 28.8 degrees 2-theta±0.2 degrees 2-theta.

In one embodiment of the present disclosure, crystalline Form A of AT-001 is isolated.

Crystalline Form A of AT-001 may be anhydrous form.

Crystalline Form A of the present disclosure as described herein, may be characterized as described in any aspect or embodiment herein, and additionally characterized by a melting point of: about 200° C. to about 204° C., about 201° C. to about 203.5° C., about 202° C. to about 203° C., or about 202.6° C., preferably as measured by DSC.

Crystalline Form A of AT-001 may be characterized by each of the above characteristics alone/or by all possible combinations, e.g., an XRPD pattern having peaks at 9.8, 19.0, 19.9, 25.2 and 28.8 degrees 2-theta±0.2 degrees 2-theta; an XRPD pattern as depicted in FIG. 1, and combinations thereof.

Figure 2:
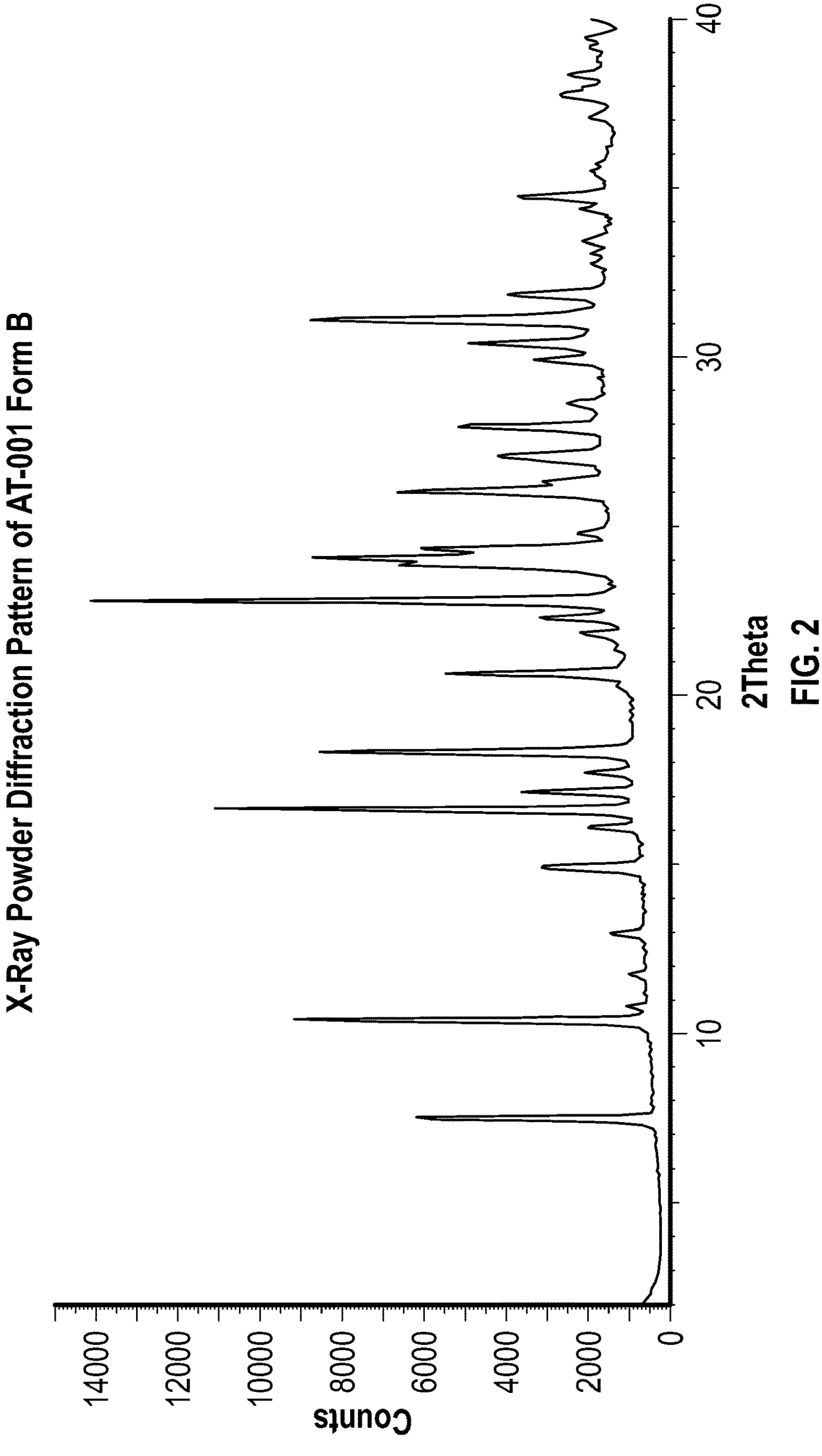
FIG. 2 shows a characteristic XRPD of AT-001 Form B.
Figure 16A:
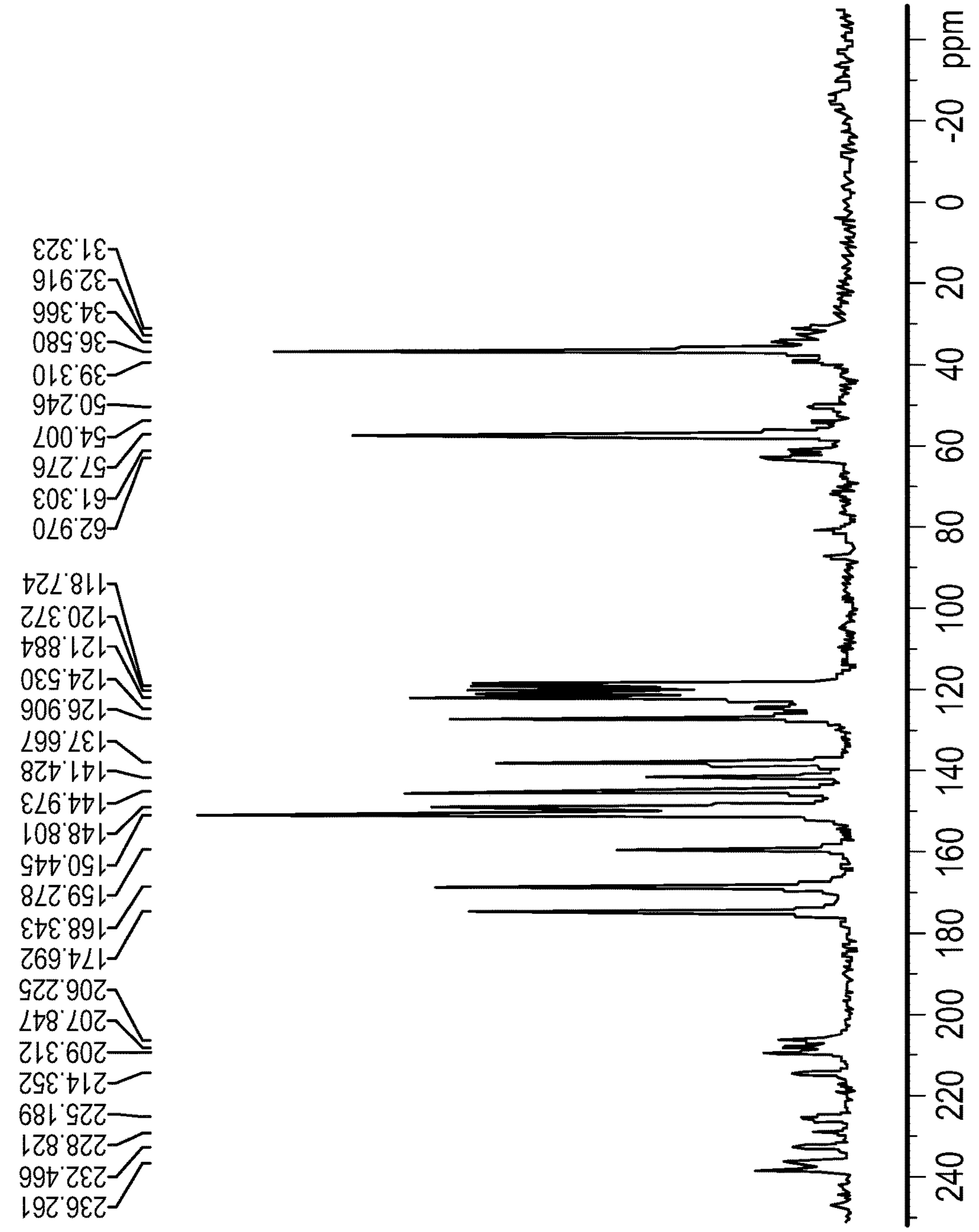
FIG. 16*a* shows $^{13}C$ solid state NMR spectrum of Form B of AT-001 (full scan).
Figure 16B:
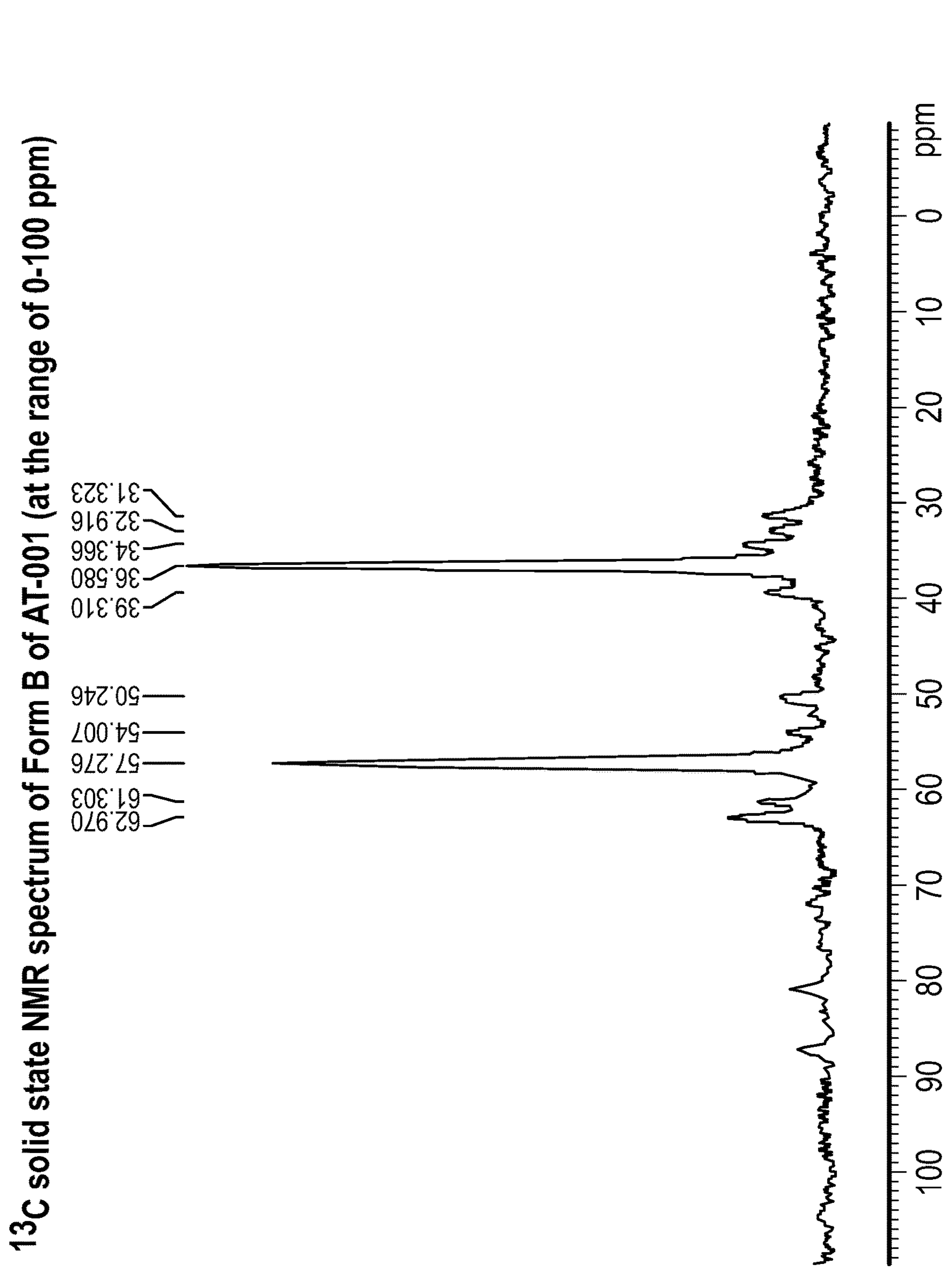
FIG. 16*b* shows $^{13}C$ solid state NMR spectrum of Form B of AT-001 (at the range of 0-100 ppm).
Figure 16C:
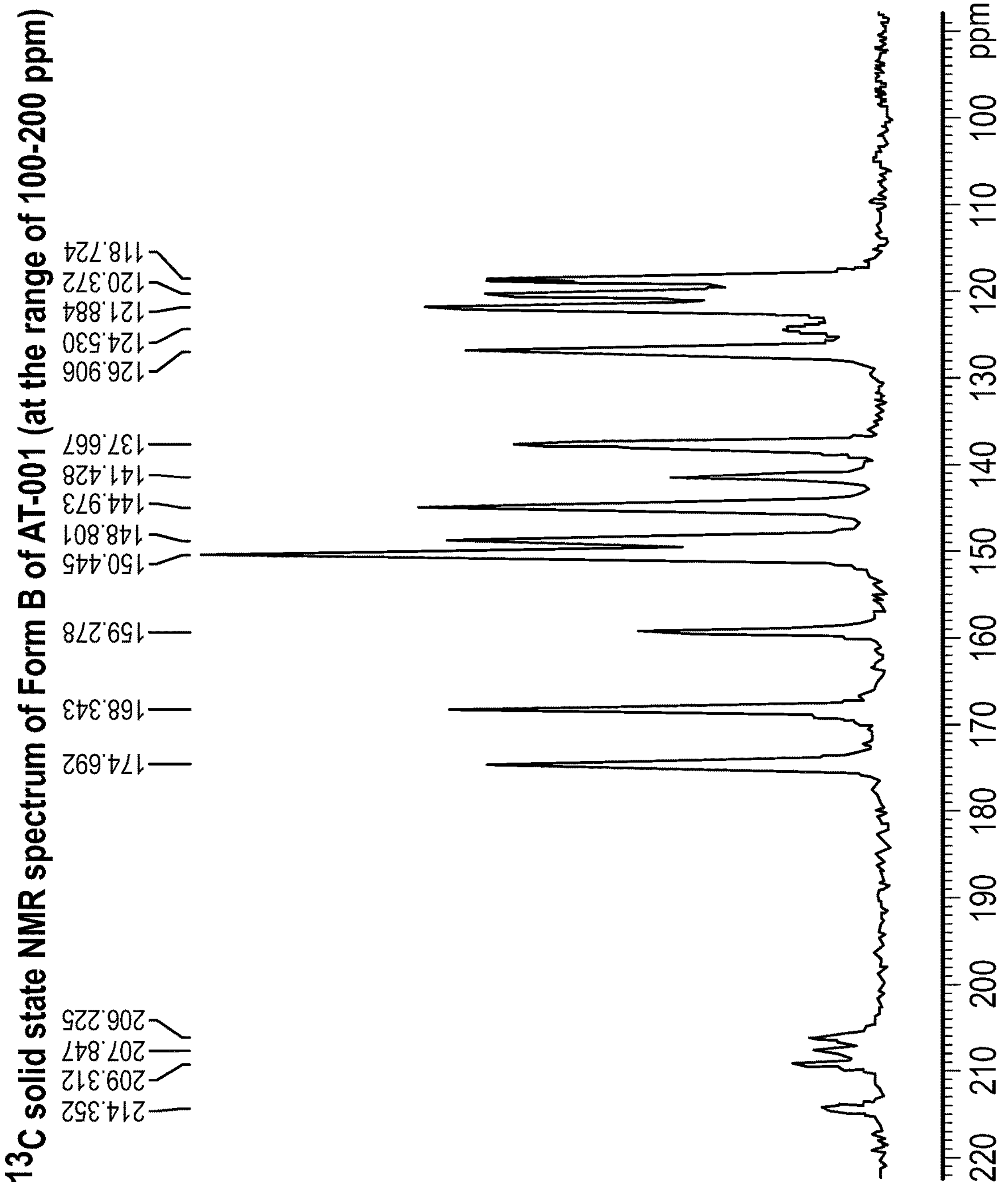
FIG. 16*c* shows $^{13}C$ solid state NMR spectrum of Form B of AT-001 (at the range of 100-200 ppm).

The present disclosure includes a crystalline polymorph of AT-001, designated Form B. The crystalline Form B of AT-001 may be characterized by data selected from one or more of the following: an X-ray powder diffraction pattern substantially as depicted in FIG. 2; an X-ray powder diffraction pattern having peaks at 7.5, 16.6, 17.1, 27.9 and 31.1 degrees 2-theta±0.2 degrees 2-theta; a solid state $^{13}C$ NMR spectrum having peaks at 36.6, 57.3, 118.7, 145, 148.8 and 168.3 ppm±0.2 ppm±0.2 ppm; a solid state $^{13}C$ NMR spectrum having the following chemical shift absolute differences from a reference peak at 34.4 ppm±2 ppm of 2.2, 22.9, 84.3, 110.6, 114.4 and 133.9 ppm±0.1 ppm; a solid state $^{13}C$ NMR spectrum substantially as depicted in FIG. 16*a*, 16*b* or 16*c*; and combinations of these data; and combinations of these data.

Crystalline Form B of AT-001 may be further characterized by an X-ray powder diffraction pattern having peaks at 7.5, 16.6, 17.1, 27.9 and 31.1 degrees 2-theta±0.2 degrees 2-theta, and also having any one, two, three, or four additional peaks selected from 10.4, 18.3, 20.6 and 26.0 degrees 2-theta±0.2 degrees 2-theta.

Crystalline Form B of AT-001 may be alternatively characterized by an X-ray powder diffraction pattern having peaks at 7.5, 10.4, 16.6, 17.1, 18.3, 20.6, 26.0, 27.9 and 31.1 degrees 2-theta±0.2 degrees 2-theta.

In one embodiment of the present disclosure, crystalline Form B of AT-001 is isolated.

Crystalline Form B of AT-001 may be hydrate form, more preferably trihydrate form. Form B according to any aspect or embodiment of the present disclosure, Form B may be further characterized by a water content of AT-001 is from about 8% to about 12% (w/w), preferably as measured by as TGA.

Crystalline Form B of AT-001 may be characterized by each of the above characteristics alone/or by all possible combinations, e.g., an XRPD pattern having peaks at 7.5, 16.6, 17.1, 27.9 and 31.1 degrees 2-theta±0.2 degrees 2-theta; an XRPD pattern as depicted in FIG. 2, and combinations thereof.

The present disclosure further comprises processes for preparation of Form B of AT-001.

Form B of AT-001 as described in any of the aspects and embodiments disclosed herein may be prepared by (a) providing a solution of AT-001 in an organic solvent, (b) combining the solution with water; and (c) optionally isolating the Form B of AT-001. Particularly Form B of AT-001 may be prepared by (a) providing a solution of AT-001 in an organic solvent, (b) combining the solution with precooled water, and (c) optionally isolating the Form B of AT-001.

In one embodiment, the process may comprise:

a) providing a solution of AT-001 in an organic solvent;

b) adding the solution into precooled water; and c) isolating the Form B of AT-001.

In any aspect or embodiment of the process for preparing Form B described herein, the solvent in step (a) may be 1,4-dioxane, formic acid or tetrahydrofuran.

In any embodiment of the process, the solution in step (a) may be at a temperature of about 40° C. to about 80° C., or about 50° C. to about 70° C., or about 60° C.

In any embodiment of the process, in step (b), the solution of step (a) may be added into precooled water at temperature of about 40° C. to about 80° C., or about 50° C. to about 70° C., or about 60° C.

In any embodiment of the process, water may be precooled in step (b) to temperature of about −5° C. to about 10° C., or about-2° C. to about 7° C., or about 0° C. to about 5° C. and the reaction mixture in step (b) may be maintained to a temperature of about −5° C. to about 10° C., or about −2° C. to about 7° C., or about 0° C. to about 5° C. After the combining or adding step (b), the mixture may be stirred for period of about 1 hour to about 4 hours, about 1.5 hours to about 3 hours, or about 2 hours, preferably at a temperature of about −5° C. to about 10° C., or about-2° C. to about 7° C., or about 0° C. to about 5° C.

In any embodiment of this process, step (c) may comprise isolating the resulting slurry by any suitable process, for example, by filtration or centrifuge. In any embodiment of the process, step (c) may comprise filtering the obtained slurry at temperature of about 15° C. to about 40° C., or about 20° C. to about 30° C., or about 25° C. for period of about 5 minutes to about 20 minutes, 5 minutes to about 15 minutes, or about 10 minutes.

In any embodiment of this process, the solvent in step (a) may typically be used in an amount of about 5 ml to about 30 ml, about 8 ml to about 25 ml, or about 10 ml to 20 ml per gram of AT-001.

In any embodiment of this process, water in step (b) may be may typically be used in an amount of about 75 ml to about 125 ml, about 90 ml to about 110 ml, or about 100 ml per gram of AT-001.

In any embodiment of the process for preparing form B of AT-001, the ratio of organic solvent to water may be from: about 4:1 to about 1:15, about 3:1 to about 1:14, about 2:1 to about 1:12, or about 1.5:1 to about 1:10.

Form B of AT-001 as defined according to any aspect or embodiment of the present disclosure, may be prepared by stirring a suspension of amorphous AT-001 in water. Particularly, Form B of AT-001 may be prepared by stirring a suspension of amorphous AT-001 in water at a temperature of 20° C. or less. In embodiments, the process may comprise: (a) providing a suspension of amorphous AT-001 in water, (b) cooling the mixture, and (c) optionally isolating Form B of AT-001.

More particularly, form B may be prepared by a process comprising:

a) combining amorphous AT-001 with water to form a suspension;

b) cooling the suspension; and c) isolating the Form B of AT-001.

In any embodiment of the process, step (a) may combine amorphous AT-001 with water for example by adding the water to the AT-001. Particularly, water in step (a) may be optionally added at a temperature of about 15° C. to about 40° C., or about 18° C. to about 30° C., or about 20° C. to about 25° C.

The suspension of amorphous AT-001 may be stirred at a temperature of about −5° C. to about 10° C., or about −2° C. to about 7° C., or about 0° C. to about 5° C., for a sufficient period of time to prepare Form B of AT-001.

In any embodiment of the process, the suspension in step (b) may be cooled to a temperature of about −5° C. to about 10° C., or about −2° C. to about 7° C., or about 0° C. to about 5° C. The suspension in step (b) may be maintained at a temperature of about −5° C. to about 10° C., or about −2° C. to about 7° C., or about 0° C. to about 5° C., preferably for period of about 30 minutes to about 60 minutes, about 35 minutes to about 55 minutes, or about 45 minutes.

In any embodiment of this process, step (c) may comprise isolating the resulting slurry by any suitable process, for example, by filtration or centrifuge. In any embodiment of the process, step (c) may comprise filtering the slurry for period of about 30 minutes to about 60 minutes, about 20 minutes to about 40 minutes, or about 15 minutes.

In any embodiment of this process, water in step (a) may typically be used in an amount of about 10 ml to about 30 ml, about 15 ml to about 25 ml, or about 20 ml per gram of AT-001.

In any aspect or embodiment of the processes for preparing form B of AT-001, the processes may further comprise combining the isolated form B AT-001 with at least one pharmaceutically acceptable excipient to form a pharmaceutical composition or pharmaceutical formulation, preferably a pharmaceutical dosage form.

Figure 3:
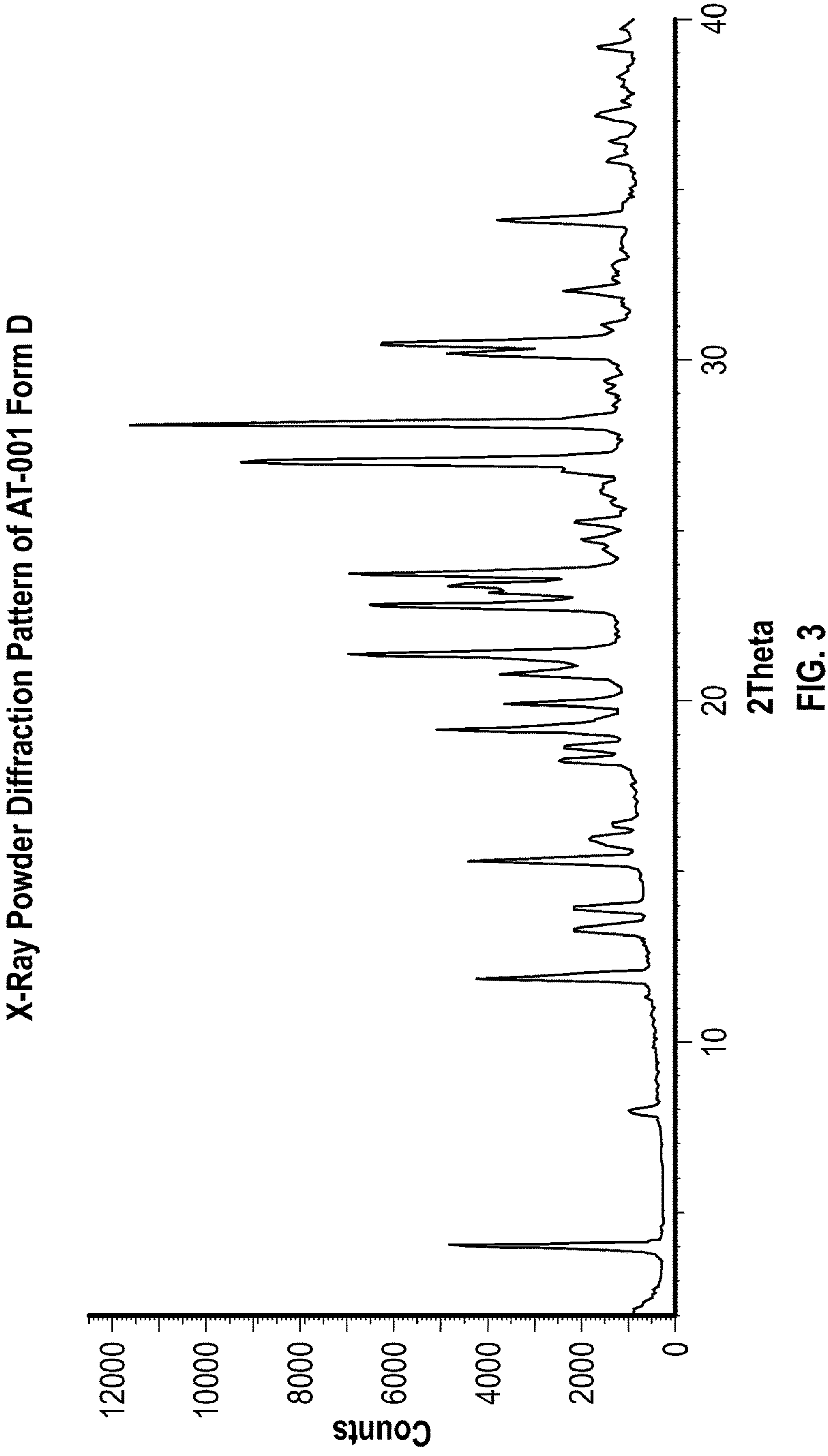
FIG. 3 shows a characteristic XRPD of AT-001 Form D.

The present disclosure includes a crystalline polymorph of AT-001, designated Form D. The crystalline Form D of AT-001 may be characterized by data selected from one or more of the following: an X-ray powder diffraction pattern substantially as depicted in FIG. 3; an X-ray powder diffraction pattern having peaks at 4.0, 11.9, 13.3, 14.0 and 15.4 degrees 2-theta #0.2 degrees 2-theta; and combinations of these data.

Crystalline Form D of AT-001 may be further characterized by an X-ray powder diffraction pattern having peaks at 4.0, 11.9, 13.3, 14.0 and 15.4 degrees 2-theta±0.2 degrees 2-theta, and also having any one, two, or three additional peaks selected from 21.4, 23.8 and 28.1 degrees 2-theta±0.2 degrees 2-theta.

Crystalline Form D of AT-001 may be alternatively characterized by an X-ray powder diffraction pattern having peaks at 4.0, 11.9, 13.3, 14.0, 15.4, 21.4, 23.8 and 28.1 degrees 2-theta±0.2 degrees 2-theta.

In one embodiment of the present disclosure, crystalline Form D of AT-001 is isolated.

Crystalline Form D of AT-001 may be solvate form, more preferably hemi Isopropyl acetate solvate.

Crystalline Form D of AT-001 may be characterized by each of the above characteristics alone/or by all possible combinations, e.g., an XRPD pattern having peaks at 4.0, 11.9, 13.3, 14.0 and 15.4 degrees 2-theta±0.2 degrees 2-theta; an XRPD pattern as depicted in FIG. 3, and combinations thereof.

Figure 5:
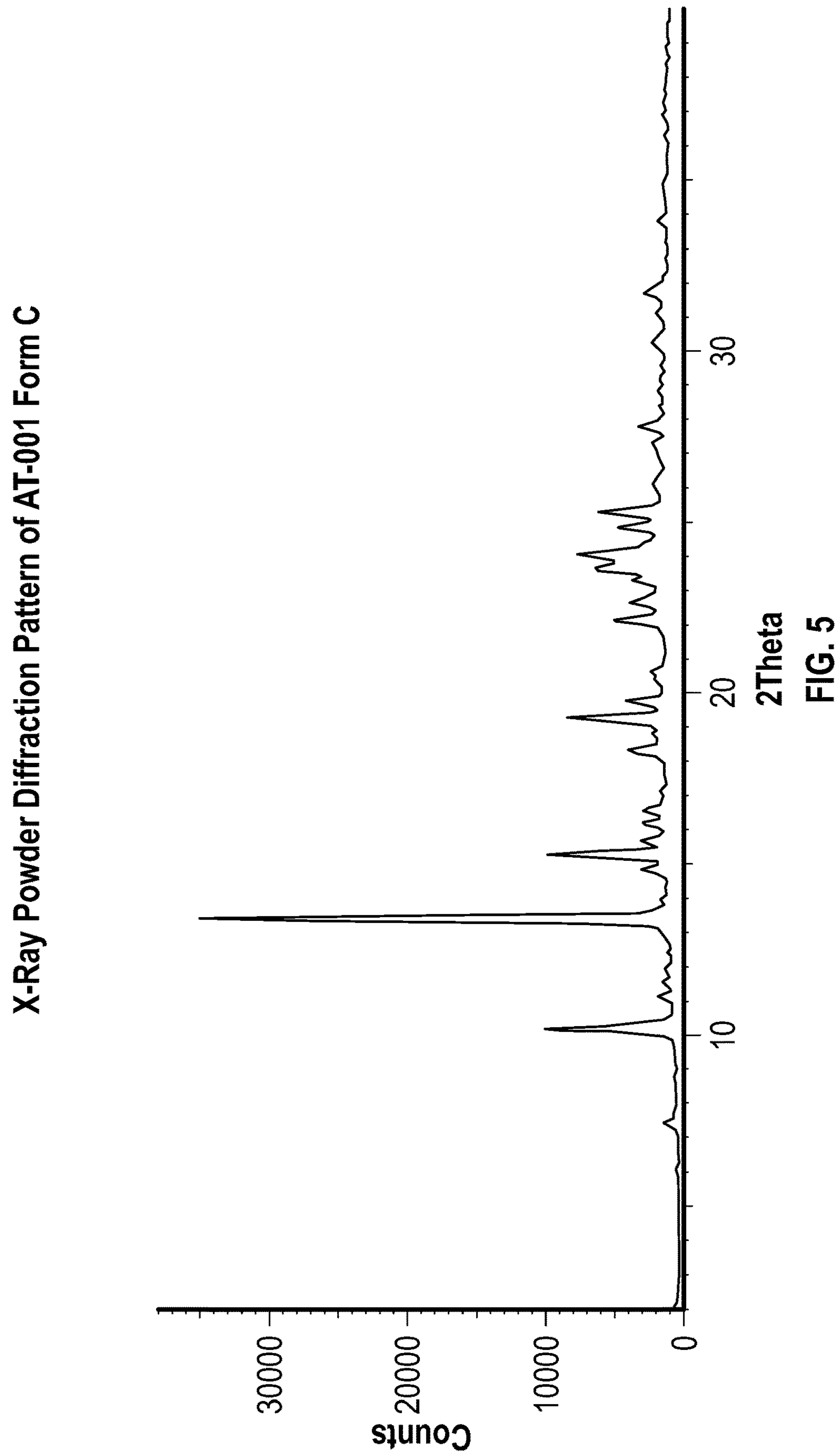
FIG. 5 shows a characteristic XRPD of AT-001 Form C.

The present disclosure includes a crystalline polymorph of AT-001, designated Form C. The crystalline Form C of AT-001 may be characterized by data selected from one or more of the following: an X-ray powder diffraction pattern substantially as depicted in FIG. 5; an X-ray powder diffraction pattern having peaks at 10.2, 13.4, 15.3, 19.3 and 25.3 degrees 2-theta±0.2 degrees 2-theta; and combinations of these data.

Crystalline Form C of AT-001 may be further characterized by an X-ray powder diffraction pattern having peaks at 10.2, 13.4, 15.3, 19.3 and 25.3 degrees 2-theta±0.2 degrees 2-theta, and also having any one, two, or three additional peaks selected from 19.8, 22.1 and 24.8 degrees 2-theta #0.2 degrees 2-theta.

Crystalline Form C of AT-001 may be alternatively characterized by an X-ray powder diffraction pattern having peaks at 10.2, 13.4, 15.3, 19.3, 19.8, 22.1, 24.8 and 25.3 degrees 2-theta±0.2 degrees 2-theta.

In one embodiment of the present disclosure, crystalline Form C of AT-001 is isolated.

Crystalline Form C of AT-001 may be hydrate.

Crystalline Form C of AT-001 may be characterized by each of the above characteristics alone/or by all possible combinations, e.g., an XRPD pattern having peaks at 10.2, 13.4, 15.3, 19.3 and 25.3 degrees 2-theta±0.2 degrees 2-theta; an XRPD pattern as depicted in FIG. 5, and combinations thereof.

Figure 6:
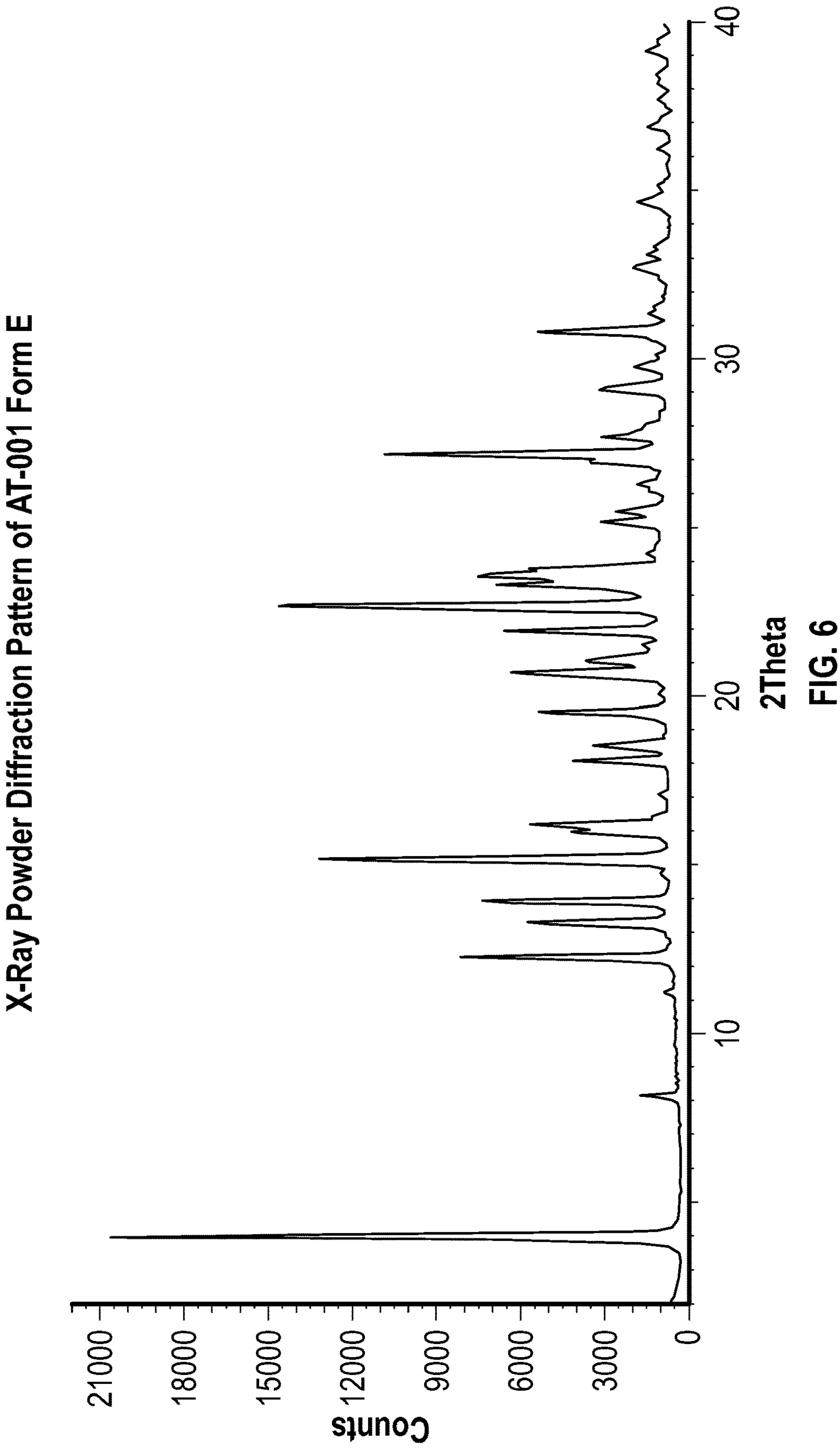
FIG. 6 shows a characteristic XRPD of AT-001 Form E.

The present disclosure includes a crystalline polymorph of AT-001, designated Form E. The crystalline Form E of AT-001 may be characterized by data selected from one or more of the following: an X-ray powder diffraction pattern substantially as depicted in FIG. 6; an X-ray powder diffraction pattern having peaks at 4.0, 8.1, 12.3, 13.9 and 27.2 degrees 2-theta±0.2 degrees 2-theta; and combinations of these data.

Crystalline Form E of AT-001 may be further characterized by an X-ray powder diffraction pattern having peaks at 4.0, 8.1, 12.3, 13.9 and 27.2 degrees 2-theta±0.2 degrees 2-theta, and also having any one, two, three or four additional peaks selected from 13.3, 15.2, 22.7 and 30.8 degrees 2-theta±0.2 degrees 2-theta.

Crystalline Form E of AT-001 may be alternatively characterized by an X-ray powder diffraction pattern having peaks at 4.0, 8.1, 12.3, 13.3, 13.9, 15.2, 22.7, 27.2 and 30.8 degrees 2-theta±0.2 degrees 2-theta.

In one embodiment of the present disclosure, crystalline Form E of AT-001 is isolated.

Crystalline Form E of AT-001 may be solvate form, more preferably ethanol solvate.

Crystalline Form E of AT-001 may be characterized by each of the above characteristics alone/or by all possible combinations, e.g., an XRPD pattern having peaks at 4.0, 8.1, 12.3, 13.9 and 27.2 degrees 2-theta±0.2 degrees 2-theta; an XRPD pattern as depicted in FIG. 6, and combinations thereof.

Figure 7:
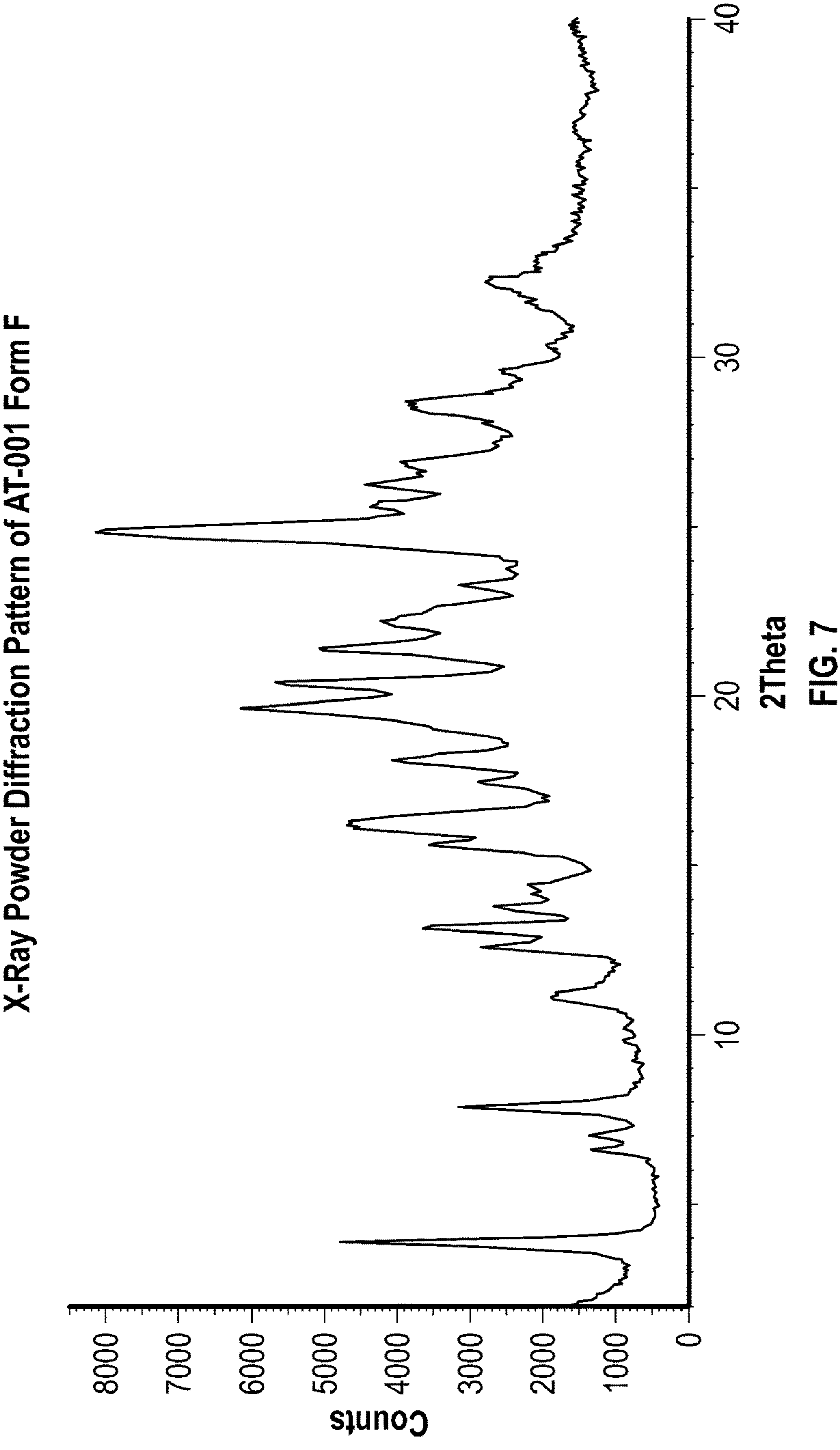
FIG. 7 shows a characteristic XRPD of AT-001 Form F.

The present disclosure includes a crystalline polymorph of AT-001, designated Form F. The crystalline Form F of AT-001 may be characterized by data selected from one or more of the following: an X-ray powder diffraction pattern substantially as depicted in FIG. 7; an X-ray powder diffraction pattern having peaks at 3.8, 7.8, 13.1, 20.3 and 24.8 degrees 2-theta±0.2 degrees 2-theta; and combinations of these data.

Crystalline Form F of AT-001 may be further characterized by an X-ray powder diffraction pattern having peaks at 3.8, 7.8, 13.1, 20.3 and 24.8 degrees 2-theta±0.2 degrees 2-theta, and also having any one, two, or three additional peaks selected from 16.2, 19.6 and 21.3 degrees 2-theta±0.2 degrees 2-theta.

Crystalline Form F of AT-001 may be alternatively characterized by an X-ray powder diffraction pattern having peaks at 3.8, 7.8, 13.1, 16.2, 19.6, 20.3, 21.3 and 24.8 degrees 2-theta±0.2 degrees 2-theta.

In one embodiment of the present disclosure, crystalline Form F of AT-001 is isolated.

Crystalline Form F of AT-001 may be solvate form, more preferably Diisopropyl ether Solvate.

Crystalline Form F of AT-001 may be characterized by each of the above characteristics alone/or by all possible combinations, e.g., an XRPD pattern having peaks at 3.8, 7.8, 13.1, 20.3 and 24.8 degrees 2-theta±0.2 degrees 2-theta; an XRPD pattern as depicted in FIG. 7, and combinations thereof.

Figure 8:
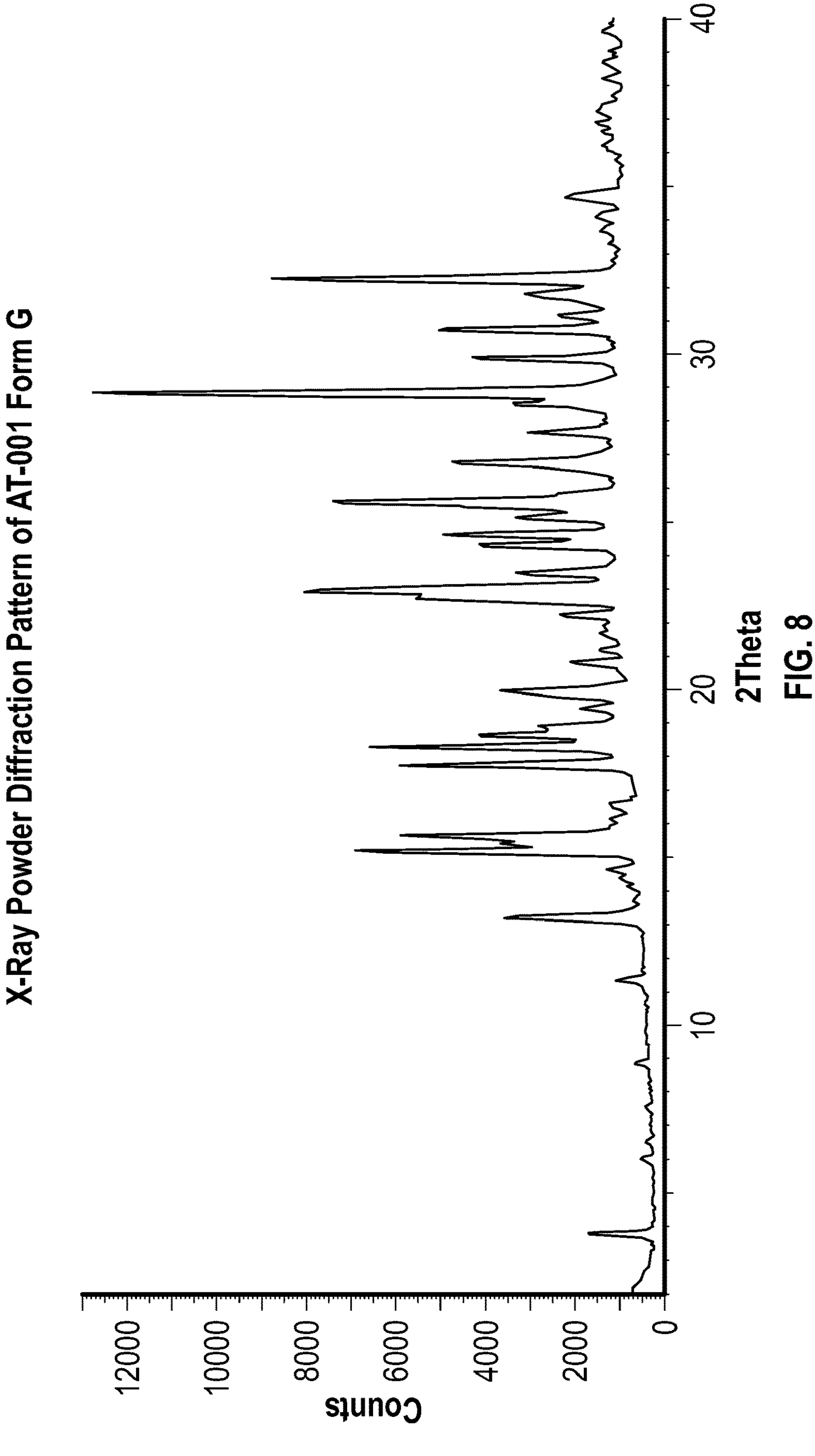
FIG. 8 shows a characteristic XRPD of AT-001 Form G.

The present disclosure includes a crystalline polymorph of AT-001, designated Form G. The crystalline Form G of AT-001 may be characterized by data selected from one or more of the following: an X-ray powder diffraction pattern substantially as depicted in FIG. 8; an X-ray powder diffraction pattern having peaks at 13.2, 25.6, 28.8, 30.7 and 32.3 degrees 2-theta±0.2 degrees 2-theta; and combinations of these data.

Crystalline Form G of AT-001 may be further characterized by an X-ray powder diffraction pattern having peaks at 13.2, 25.6, 28.8, 30.7 and 32.3 degrees 2-theta±0.2 degrees 2-theta, and also having any one, two, three, or four additional peaks selected from 15.2, 15.6, 17.8 and 29.9 degrees 2-theta±0.2 degrees 2-theta.

Crystalline Form G of AT-001 may be alternatively characterized by an X-ray powder diffraction pattern having peaks at 13.2, 15.2, 15.6, 17.8, 25.6, 28.8, 29.9, 30.7 and 32.3 degrees 2-theta±0.2 degrees 2-theta.

In one embodiment of the present disclosure, crystalline Form G of AT-001 is isolated.

Crystalline Form G of AT-001 may be solvate form, more preferably Dimethyl Formamide Solvate.

Crystalline Form G of AT-001 may be characterized by each of the above characteristics alone/or by all possible combinations, e.g., an XRPD pattern having peaks at 13.2, 25.6, 28.8, 30.7 and 32.3 degrees 2-theta±0.2 degrees 2-theta; an XRPD pattern as depicted in FIG. 8, and combinations thereof.

Figure 9:
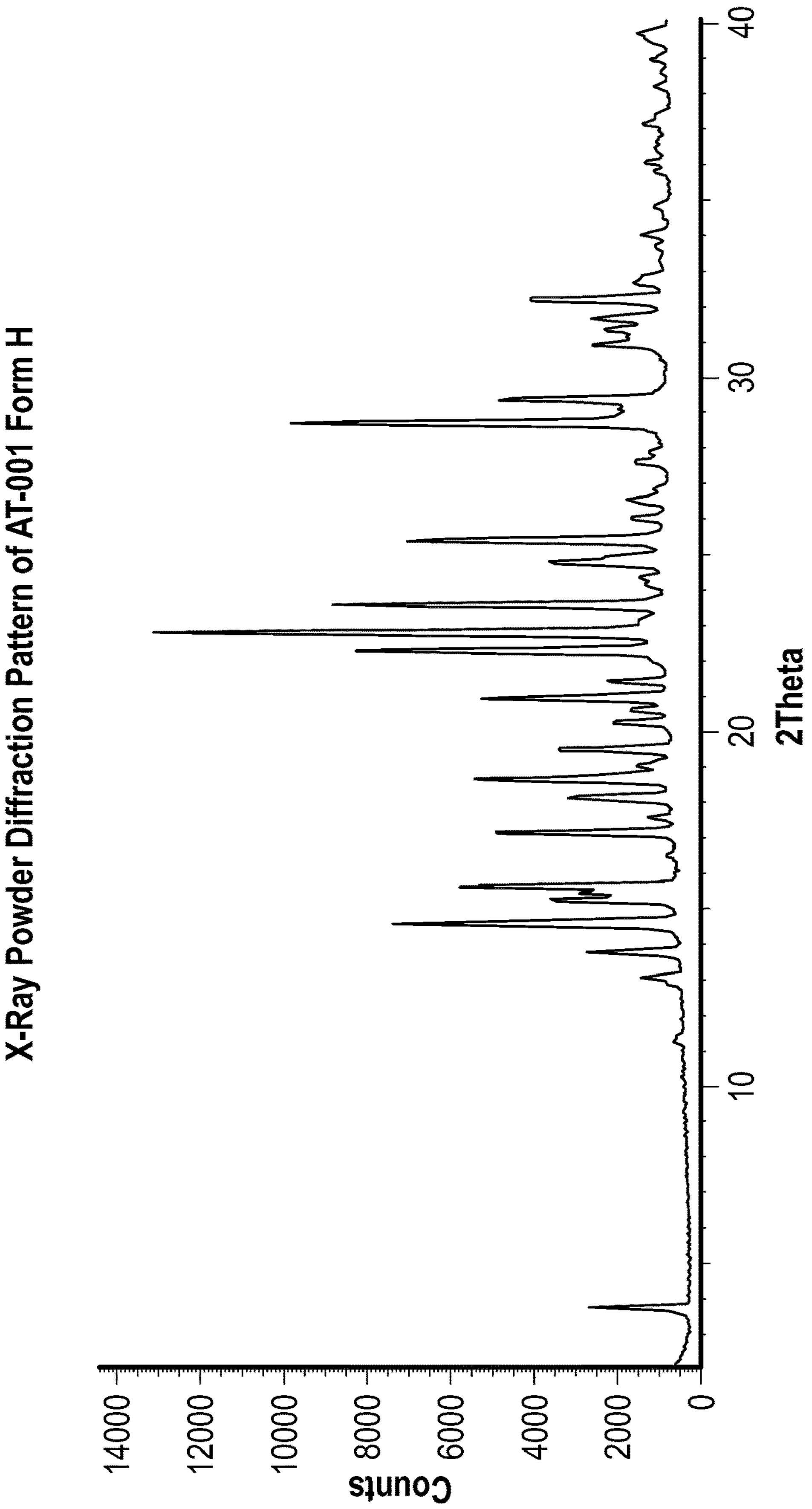
FIG. 9 shows a characteristic XRPD of AT-001 Form H.

The present disclosure includes a crystalline polymorph of AT-001, designated Form H. The crystalline Form H of AT-001 may be characterized by data selected from one or more of the following: an X-ray powder diffraction pattern substantially as depicted in FIG. 9; an X-ray powder diffraction pattern having peaks at 13.8, 18.7, 22.3, 23.6 and 25.4 degrees 2-theta±0.2 degrees 2-theta; and combinations of these data.

Crystalline Form H of AT-001 may be further characterized by an X-ray powder diffraction pattern having peaks at 13.8, 18.7, 22.3, 23.6 and 25.4 degrees 2-theta±0.2 degrees 2-theta, and also having any one, two, three, or four additional peaks selected from 14.6, 17.2, 22.8 and 29.4 degrees 2-theta±0.2 degrees 2-theta.

Crystalline Form H of AT-001 may be alternatively characterized by an X-ray powder diffraction pattern having peaks at 13.8, 14.6, 17.2, 18.7, 22.3, 22.8, 23.6, 25.4 and 29.4 degrees 2-theta±0.2 degrees 2-theta.

In one embodiment of the present disclosure, crystalline Form H of AT-001 is isolated.

Crystalline Form H of AT-001 may be solvate form, more preferably Dimethyl Acetamide Solvate.

Crystalline Form H of AT-001 may be characterized by each of the above characteristics alone/or by all possible combinations, e.g., an XRPD pattern having peaks at 13.8, 18.7, 22.3, 23.6 and 25.4 degrees 2-theta±0.2 degrees 2-theta; an XRPD pattern as depicted in FIG. 9, and combinations thereof.

Figure 10:
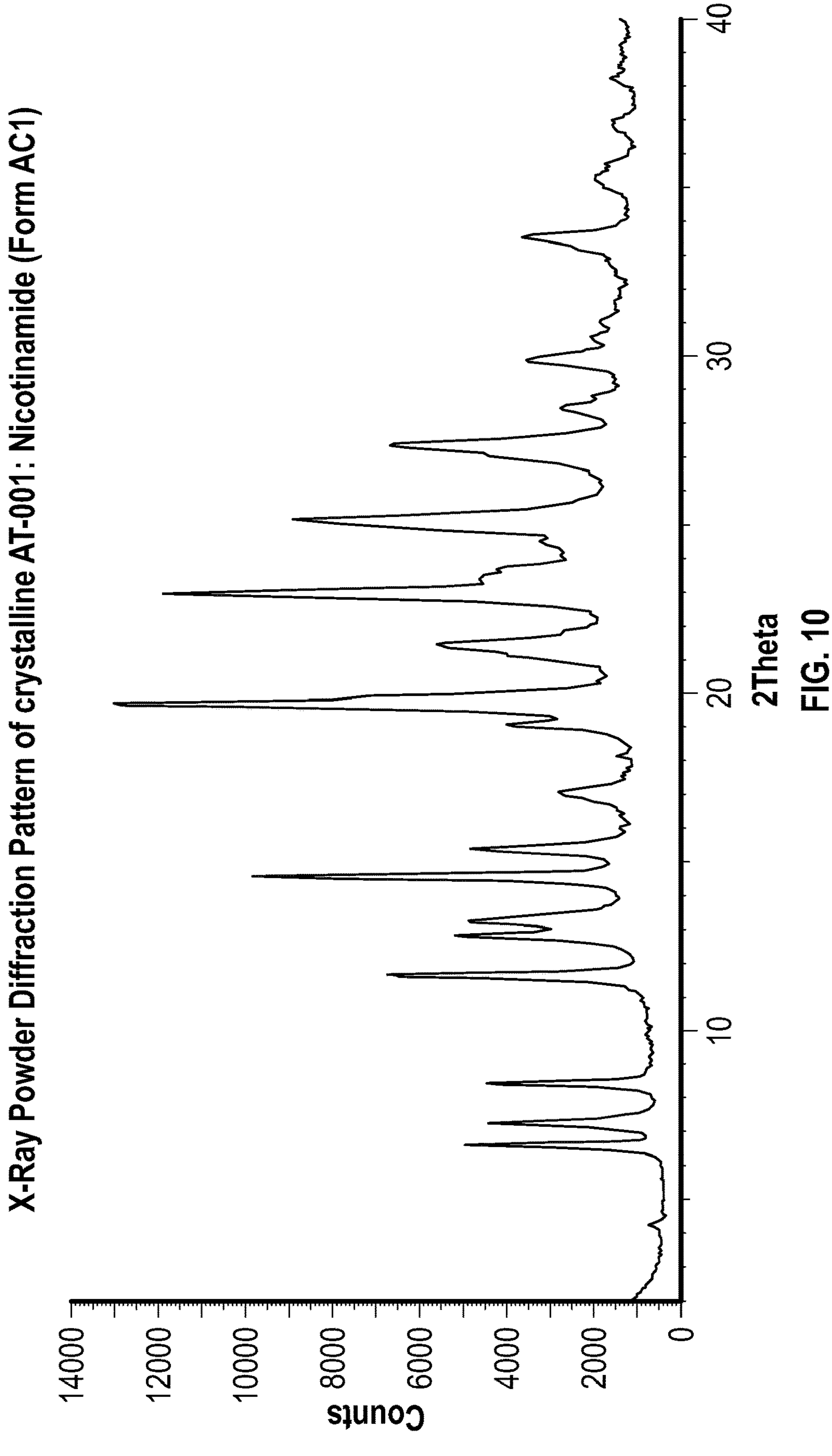
FIG. 10 shows a characteristic XRPD of Crystalline AT-001: Nicotinamide (Form AC1).

The present disclosure includes a crystalline AT-001: Nicotinamide, designated Form AC1. The crystalline Form AC1 of AT-001: Nicotinamide may be characterized by data selected from one or more of the following: an X-ray powder diffraction pattern substantially as depicted in FIG. 10; an X-ray powder diffraction pattern having peaks at 7.0, 8.2, 11.4, 12.6 and 15.2 degrees 2-theta±0.2 degrees 2-theta; and combinations of these data.

Crystalline Form AC1 of AT-001: Nicotinamide may be further characterized by an X-ray powder diffraction pattern having peaks at 7.0, 8.2, 11.4, 12.6 and 15.2 degrees 2-theta 0.2 degrees 2-theta, and also having any one, two, or three additional peaks selected from 13.1, 19.5 and 21.3 degrees 2-theta±0.2 degrees 2-theta.

Crystalline Form AC1 of AT-001 may be alternatively characterized by an X-ray powder diffraction pattern having peaks at 7.0, 8.2, 11.4, 12.6 13.1, 15.2, 19.5 and 21.3 degrees 2-theta±0.2 degrees 2-theta.

In one embodiment of the present disclosure, crystalline Form AC1 of AT-001: Nicotinamide is isolated.

Crystalline Form AC1 of AT-001: Nicotinamide may be a solvate, more preferably Hemi Acetonitrile solvate.

Crystalline Form AC1 of AT-001: Nicotinamide may be characterized by each of the above characteristics alone/or by all possible combinations, e.g., an XRPD pattern having peaks at 7.0, 8.2, 11.4, 12.6 and 15.2 degrees 2-theta±0.2 degrees 2-theta; an XRPD pattern as depicted in FIG. 10, and combinations thereof.

The above crystalline polymorph can be used to prepare other crystalline polymorphs of AT-001: Nicotinamide.

In one embodiment crystalline form AC1 of AT-001: Nicotinamide may be a co-crystal. In another embodiment crystalline form AC1 of AT-001: Nicotinamide may be a salt.

Figure 11:
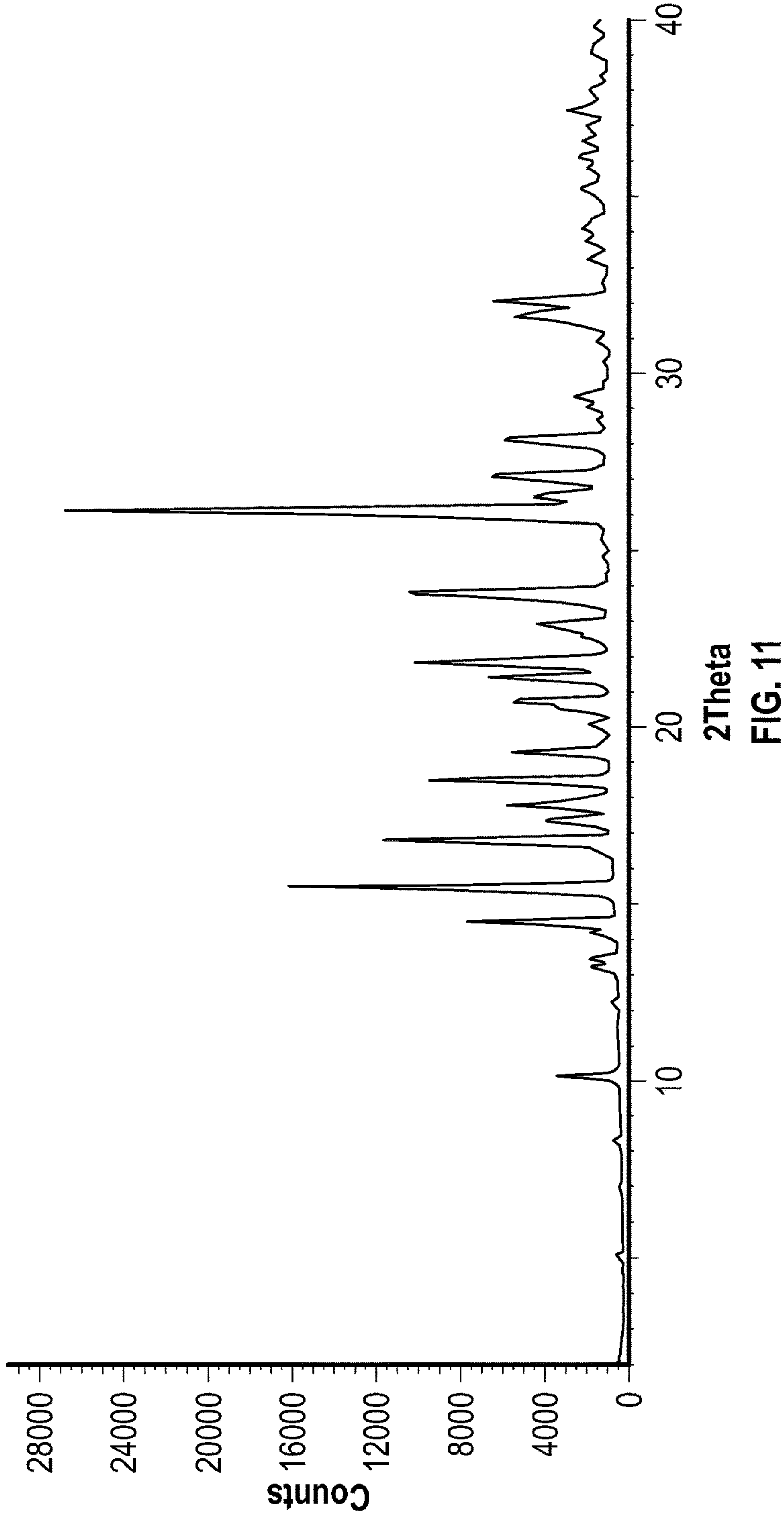
FIG. 11 shows a characteristic XRPD of Crystalline AT-001: Isonicotinamide (Form AC2).

The present disclosure includes a crystalline AT-001: Isonicotinamide, designated Form AC2. Crystalline Form AC2 of AT-001: Isonicotinamide may be characterized by data selected from one or more of the following: an X-ray powder diffraction pattern substantially as depicted in FIG. 11; an X-ray powder diffraction pattern having peaks at 14.5, 15.5, 16.8, 21.4 and 26.1 degrees 2-theta±0.2 degrees 2-theta; and combinations of these data.

Crystalline Form AC2 of AT-001: Isonicotinamide may be further characterized by an X-ray powder diffraction pattern having peaks at 14.5, 15.5, 16.8, 21.4 and 26.1 degrees 2-theta±0.2 degrees 2-theta, and also having any one, two, three or four additional peaks selected from 18.5, 21.8, 23.8 and 32.1 degrees 2-theta±0.2 degrees 2-theta.

Crystalline Form AC2 of AT-001 may be alternatively characterized by an X-ray powder diffraction pattern having peaks at 14.5, 15.5, 16.8, 18.5, 21.4, 21.8, 23.8, 26.1 and 32.1 degrees 2-theta±0.2 degrees 2-theta.

In one embodiment of the present disclosure, crystalline Form AC2 of AT-001: Isonicotinamide is isolated.

Crystalline Form AC2 of AT-001: Isonicotinamide may be hydrate, more preferably monohydrate.

Crystalline Form AC2 of AT-001: Isonicotinamide may be characterized by each of the above characteristics alone/or by all possible combinations, e.g., an XRPD pattern having peaks at 14.5, 15.5, 16.8, 21.4 and 26.1 degrees 2-theta±0.2 degrees 2-theta; an XRPD pattern as depicted in FIG. 11, and combinations thereof.

The above crystalline polymorph can be used to prepare other crystalline polymorphs of AT-001: Isonicotinamide.

In one embodiment crystalline form AC2 of AT-001: Isonicotinamide may be a co-crystal. In another embodiment crystalline form AC2 of AT-001: Isonicotinamide may be a salt.

Figure 12:
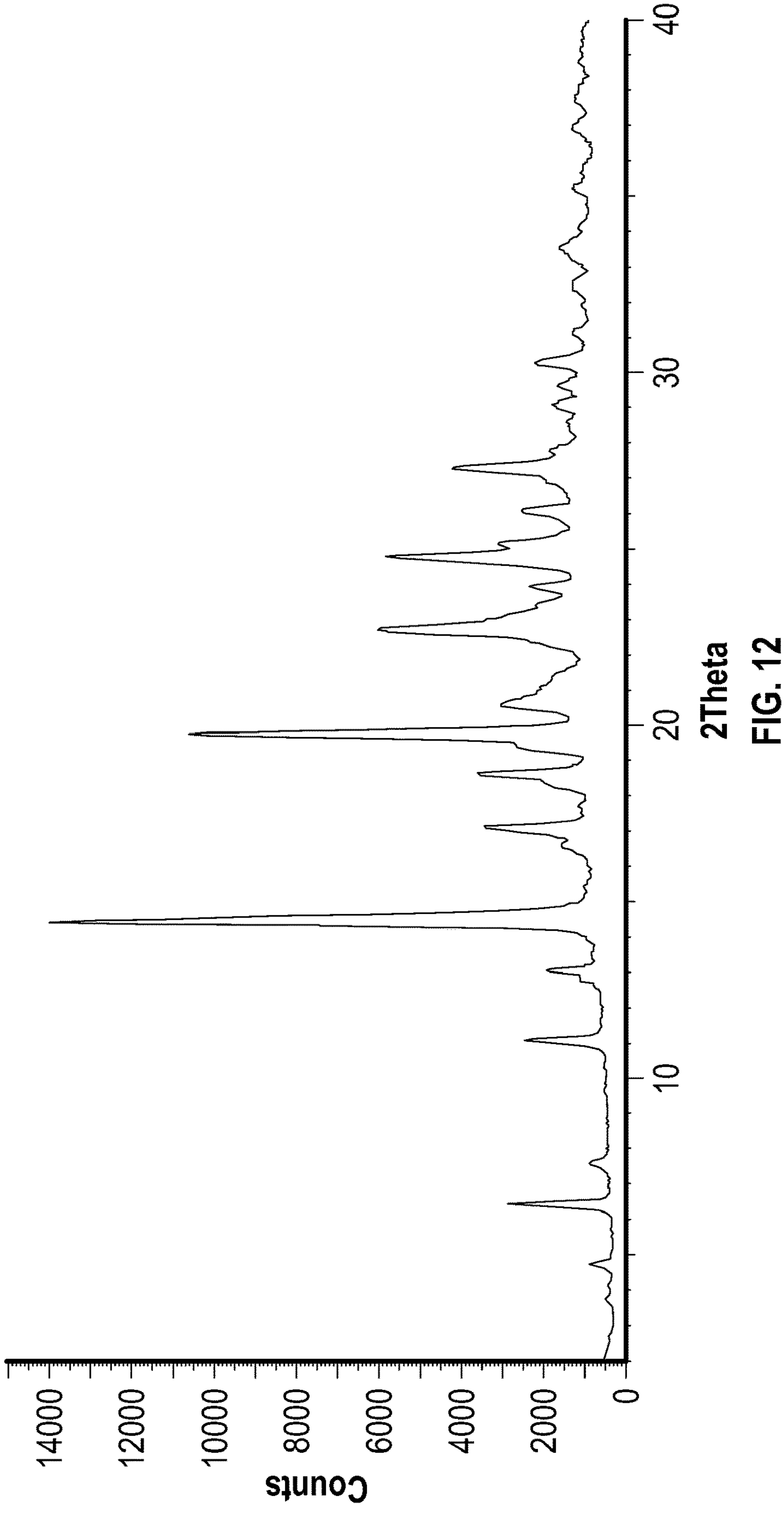
FIG. 12 shows a characteristic XRPD of Crystalline AT-001: Nicotinamide (Form AC3).

The present disclosure includes a crystalline AT-001: Nicotinamide, designated Form AC3. Crystalline Form AC3 of AT-001: Nicotinamide may be characterized by data selected from one or more of the following: an X-ray powder diffraction pattern substantially as depicted in FIG. 12; an X-ray powder diffraction pattern having peaks at 6.5, 11.1, 14.5, 17.1 and 23.9 degrees 2-theta±0.2 degrees 2-theta; and combinations of these data.

Crystalline Form AC3 of AT-001: Nicotinamide may be further characterized by an X-ray powder diffraction pattern having peaks at 6.5, 11.1, 14.5, 17.1 and 23.9 degrees 2-theta±0.2 degrees 2-theta, and also having any one, two, three or four additional peaks selected from 19.8, 22.7, 24.8 and 27.3 degrees 2-theta±0.2 degrees 2-theta.

Crystalline Form AC3 of AT-001 may be alternatively characterized by an X-ray powder diffraction pattern having peaks at 6.5, 11.1, 14.5, 17.1, 19.8, 22.7, 23.9, 24.8 and 27.3 degrees 2-theta±0.2 degrees 2-theta.

In one embodiment of the present disclosure, crystalline Form AC3 of AT-001: Nicotinamide is isolated.

Crystalline Form AC3 of AT-001: Nicotinamide may be anhydrous.

Crystalline Form AC3 of AT-001: Nicotinamide may be characterized by each of the above characteristics alone/or by all possible combinations, e.g., an XRPD pattern having peaks at 6.5, 11.1, 14.5, 17.1 and 23.9 degrees 2-theta±0.2 degrees 2-theta; an XRPD pattern as depicted in FIG. 12, and combinations thereof.

The above crystalline polymorph can be used to prepare other crystalline polymorphs of AT-001: Nicotinamide.

In one embodiment crystalline form AC3 of AT-001: Nicotinamide may be a co-crystal. In another embodiment crystalline form AC1 of AT-001: Nicotinamide may be a salt.

Figure 13:
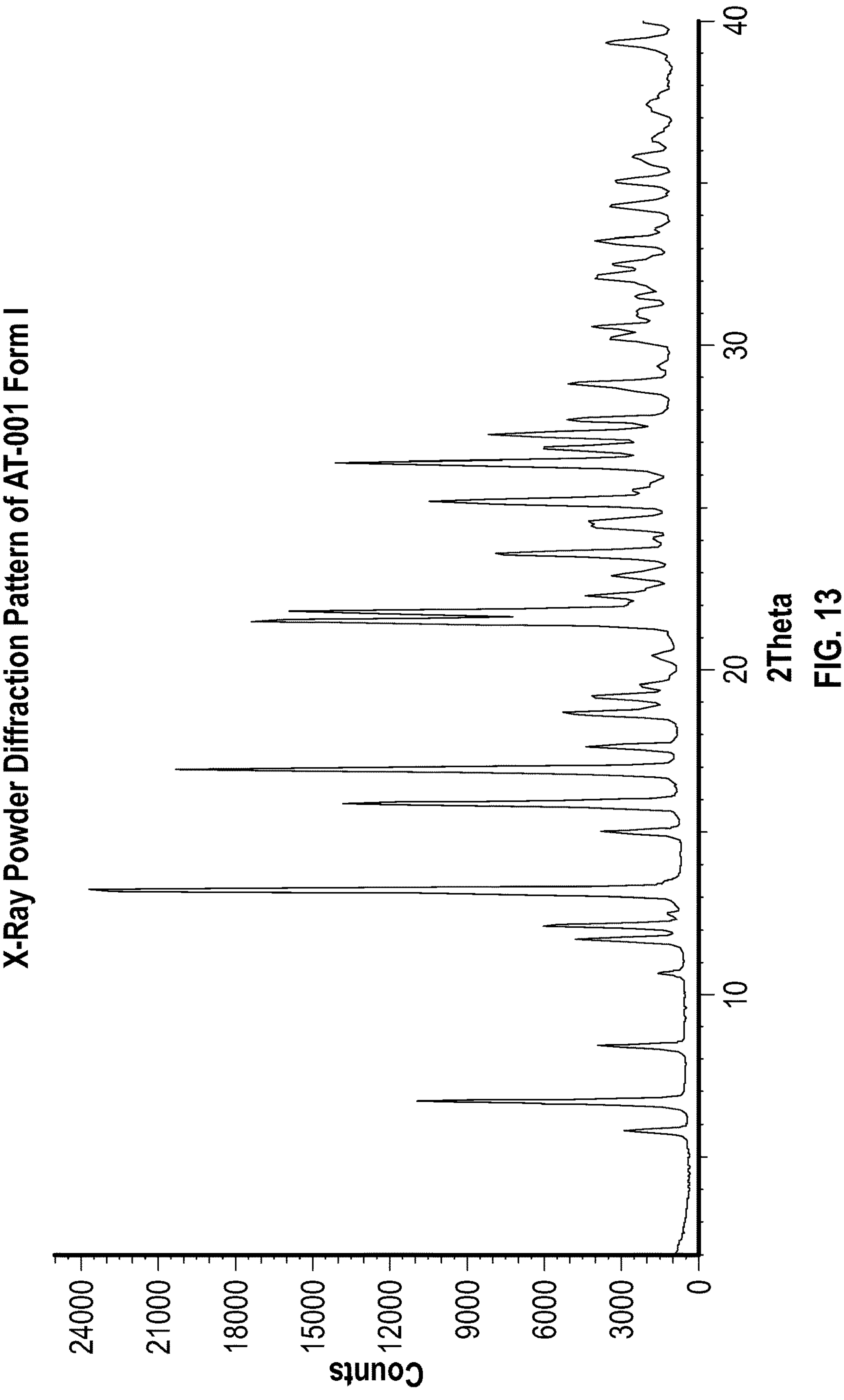
FIG. 13 shows a characteristic XRPD of AT-001 Form I.

The present disclosure includes a crystalline polymorph of AT-001, designated Form I. The crystalline Form I of AT-001 may be characterized by data selected from one or more more of the following: an X-ray powder diffraction pattern substantially as depicted in FIG. 13; an X-ray powder diffraction pattern having peaks at 6.7, 8.4, 13.2, 15.9 and 18.7 degrees 2-theta±0.2 degrees 2-theta; and combinations of these data.

Crystalline Form I of AT-001 may be further characterized by an X-ray powder diffraction pattern having peaks at 6.7, 8.4, 13.2, 15.9 and 18.7 degrees 2-theta±0.2 degrees 2-theta, and also having any one, two, three, or four additional peaks selected from 12.1, 16.9, 21.5 and 23.6 degrees 2-theta±0.2 degrees 2-theta.

Crystalline Form I of AT-001 may be alternatively characterized by an X-ray powder diffraction pattern having peaks at 6.7, 8.4, 12.1, 13.2, 15.9, 16.9, 18.7, 21.5 and 23.6 degrees 2-theta±0.2 degrees 2-theta.

In one embodiment of the present disclosure, crystalline Form I of AT-001 is isolated.

Crystalline Form I of AT-001 may be solvate form, more preferably N-Methyl Formamide Solvate.

Crystalline Form I of AT-001 may be characterized by each of the above characteristics alone/or by all possible combinations, e.g., an XRPD pattern having peaks at 6.7, 8.4, 13.2, 15.9 and 18.7 degrees 2-theta±0.2 degrees 2-theta; an XRPD pattern as depicted in FIG. 13, and combinations thereof.

Figure 14:
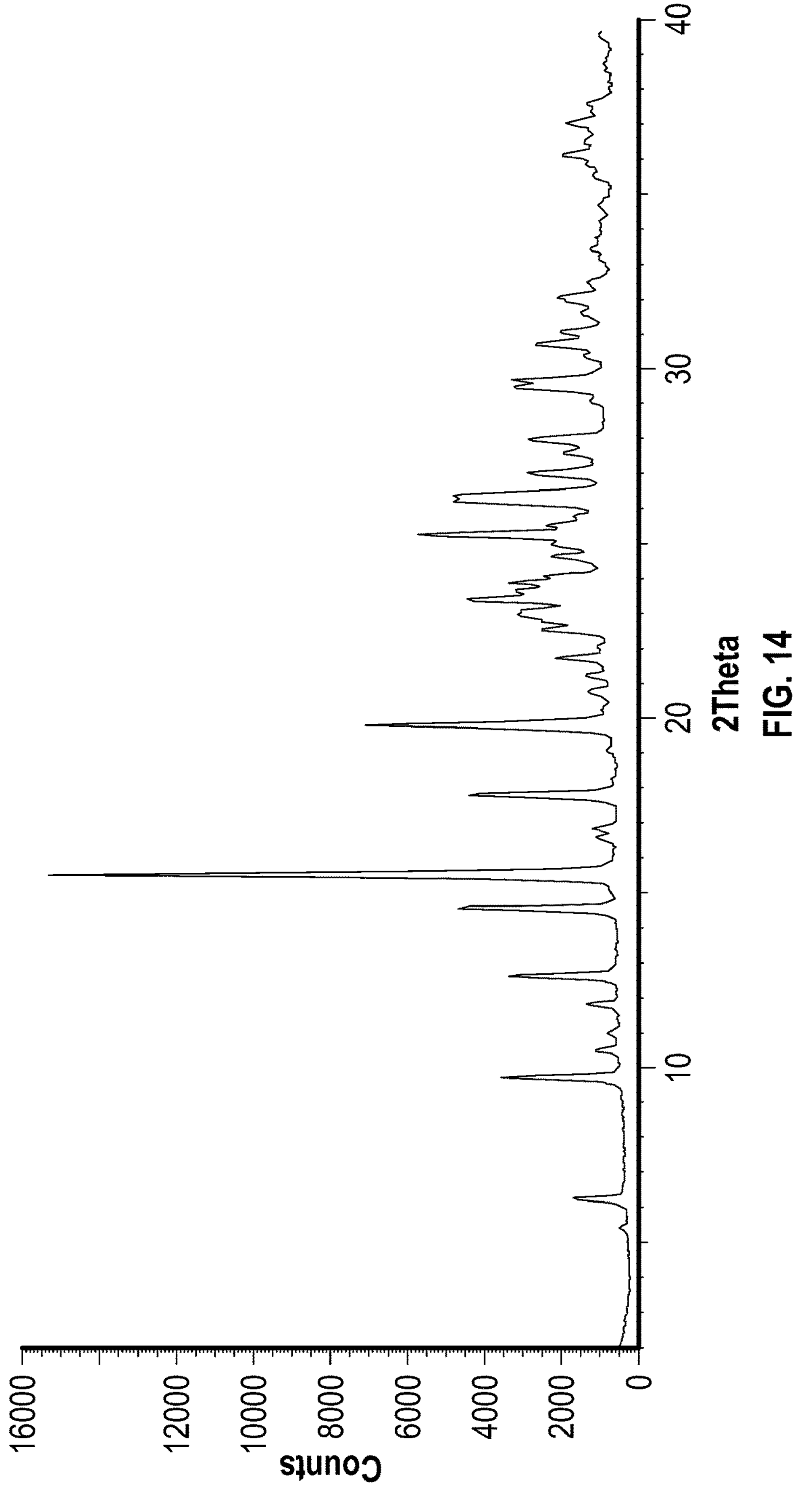
FIG. 14 shows a characteristic XRPD of AT-001 Form J.

The present disclosure includes a crystalline polymorph of AT-001, designated Form J. The crystalline Form J of AT-001 may be characterized by data selected from one or more of the following: an X-ray powder diffraction pattern substantially as depicted in FIG. 14; an X-ray powder diffraction pattern having peaks at 6.3, 9.7, 12.6, 14.6 and 15.5 degrees 2-theta±0.2 degrees 2-theta; and combinations of these data.

Crystalline Form J of AT-001 may be further characterized by an X-ray powder diffraction pattern having peaks at 6.3, 9.7, 12.6, 14.6 and 15.5 degrees 2-theta±0.2 degrees 2-theta, and also having any one, two, or three additional peaks selected from 17.8, 19.8 and 21.7 degrees 2-theta±0.2 degrees 2-theta.

Crystalline Form J of AT-001 may be alternatively characterized by an X-ray powder diffraction pattern having peaks at 6.3, 9.7, 12.6, 14.6, 15.5, 17.8, 19.8 and 21.7 degrees 2-theta±0.2 degrees 2-theta.

In one embodiment of the present disclosure, crystalline Form J of AT-001 is isolated.

Crystalline Form J of AT-001 may be solvate form, more preferably Formamide Solvate.

Crystalline Form J of AT-001 may be characterized by each of the above characteristics alone/or by all possible combinations, e.g., an XRPD pattern having peaks at 6.3, 9.7, 12.6, 14.6 and 15.5 degrees 2-theta±0.2 degrees 2-theta; an XRPD pattern as depicted in FIG. 14, and combinations thereof.

Figure 15:
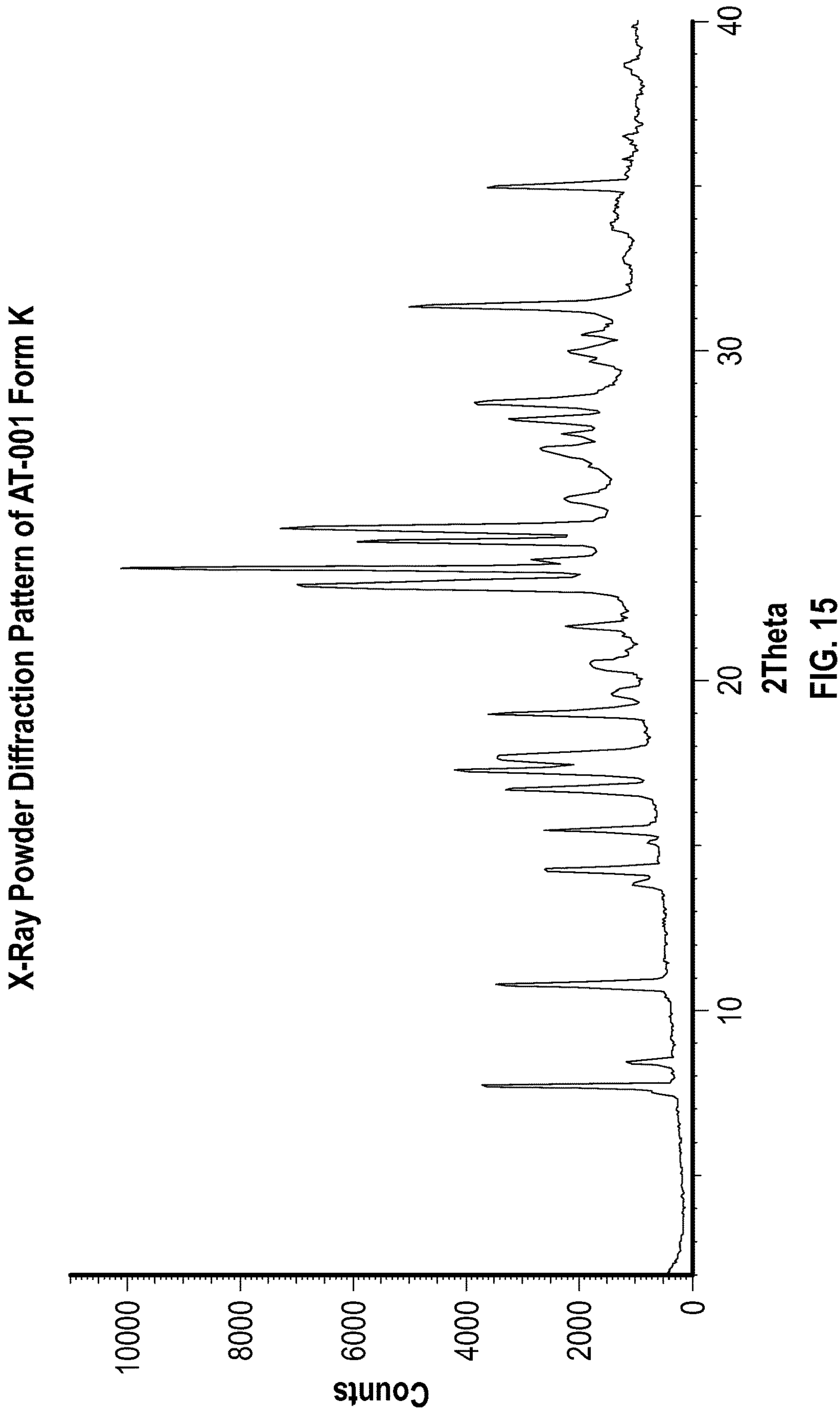
FIG. 15 shows a characteristic XRPD of AT-001 Form K.

The present disclosure includes a crystalline polymorph of AT-001, designated Form K. The crystalline Form K of AT-001 may be characterized by data selected from one or more of the following: an X-ray powder diffraction pattern substantially as depicted in FIG. 15; an X-ray powder diffraction pattern having peaks at 7.7, 8.4, 10.7, 31.3 and 34.9 degrees 2-theta±0.2 degrees 2-theta; and combinations of these data.

Crystalline Form K of AT-001 may be further characterized by an X-ray powder diffraction pattern having peaks at 7.7, 8.4, 10.7, 31.3 and 34.9 degrees 2-theta±0.2 degrees 2-theta, and also having any one, two, or three additional peaks selected from 14.2, 17.3, and 24.6 degrees 2-theta±0.2 degrees 2-theta.

Crystalline Form K of AT-001 may be alternatively characterized by an X-ray powder diffraction pattern having peaks at 7.7, 8.4, 10.7, 14.2, 17.3, 24.6, 31.3 and 34.9 degrees 2-theta±0.2 degrees 2-theta.

In one embodiment of the present disclosure, crystalline Form K of AT-001 is isolated.

Crystalline Form K of AT-001 may be solvate form, more preferably Formamide Solvate.

Crystalline Form K of AT-001 may be characterized by each of the above characteristics alone/or by all possible combinations, e.g., an XRPD pattern having peaks at 7.7, 8.4, 10.7, 31.3 and 34.9 degrees 2-theta±0.2 degrees 2-theta; an XRPD pattern as depicted in FIG. 15, and combinations thereof.

In any aspect or embodiment of the present disclosure, any of the solid state forms of AT-001, AT-001 salts, AT-001 solvates, or AT-001 cocrystals, described herein may be polymorphically pure or may be substantially free of any other solid state forms of the subject AT-001, AT-001 salts, AT-001 solvate, or AT-001 cocrystal (for example a crystalline Form F of AT-001 which is in the form of a diisopropyl ether solvate, which is polymorphically pure, may be substantially free of any other solid state forms of AT-001 Diisopropyl ether Solvate; and likewise a crystalline Form B of AT-001 which is polymorphically pure may be substantially free of any other solid state forms of AT-001). In any aspect or embodiment of the present disclosure, any of the solid state forms of AT-001, AT-001 salt, AT-001 solvate, or AT-001 cocrystals described in any aspect or embodiment disclosed herein, may be polymorphically pure or substantially free of other solid state forms of AT-001, AT-001 salt, AT-001 solvates, or AT-001 cocrystals and may contain: about 20% (w/w) or less, about 10% (w/w) or less, about 5% (w/w) or less, about 2% (w/w) or less, about 1% (w/w) or less, about 0.5% (w/w) or less, about 0.2% (w/w) or less, about 0.1% (w/w) or less, or about 0%, of any other solid state forms of the subject compound (i.e. AT-001, AT-001 salt, AT-001 solvate, or AT-001 cocrystal, respectively), preferably as measured by XRPD. Thus, any of the disclosed crystalline forms of AT-001, AT-001 salt, AT-001 solvate, or AT-001 cocrystal, described herein may be substantially free of any other solid state forms of the subject AT-001, AT-001 salt, AT-001 solvate, or AT-001 cocrystal, respectively, and may contain greater than about 80% (w/w), greater than about 90% (w/w), greater than about 95% (w/w), greater than about 98% (w/w), greater than about 99% (w/w), or about 100% of the subject solid state form of the AT-001, AT-001 salt, AT-001 solvate, or AT-001 cocrystal, respectively.

The above crystalline polymorphs as defined in any aspect or embodiment disclosed herein can be used to prepare other crystalline polymorphs of AT-001, AT-001 salts or cocrystals and their solid state forms.

The present disclosure encompasses a process for preparing other solid state forms of AT-001, AT-001 salts or co-crystals and their solid state forms thereof. The process includes preparing any one of the crystalline polymorph of AT-001 as defined in any aspect or embodiment disclosed herein by the processes of the present disclosure, and converting it to other polymorph of AT-001 or salt of AT-001.

The present disclosure provides the above described crystalline polymorphs of AT-001 as defined in any aspect or embodiment disclosed herein for use in the preparation of pharmaceutical compositions comprising AT-001 and/or crystalline polymorphs thereof.

The present disclosure also encompasses the use of crystalline polymorphs of AT-001 as defined in any aspect or embodiment of the present disclosure for the preparation of pharmaceutical compositions of crystalline polymorph AT-001 and/or crystalline polymorphs thereof.

The present disclosure includes processes for preparing the above mentioned pharmaceutical compositions. The processes include combining any one or a combination of the crystalline polymorphs of AT-001 as defined in any aspect or embodiment of the present disclosure with at least one pharmaceutically acceptable excipient.

Pharmaceutical combinations or formulations of the present disclosure contain any one or a combination of the solid state forms of AT-001 as defined in any aspect or embodiment of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, AT-001 and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of AT-001 can be administered. AT-001 may be formulated for administration to a mammal, in embodiments to a human, by injection. AT-001 can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of AT-001 and the pharmaceutical compositions and/or formulations of AT-001 of the present disclosure can be used as medicaments, in embodiments in the treatment of Diabetic Cardiomyopathy, Diabetic Peripheral Neuropathy, acute lung inflammation in critical COVID-19 patients, or cardiomyopathy in critical COVID-19 patients, and preferably Diabetic Cardiomyopathy.

The present disclosure also provides methods of treating Diabetic Cardiomyopathy, Diabetic Peripheral Neuropathy, acute lung inflammation in critical COVID-19 patients, or cardiomyopathy in critical COVID-19 patients, and preferably Diabetic Cardiomyopathy by administering a therapeutically effective amount of any one or a combination of the crystalline polymorphs of AT-001 of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

X-ray diffraction was performed on X-Ray powder diffractometer:

Bruker D8 Advance; CuKα radiation (λ=1.5418 Å); Lynx eye detector; laboratory temperature 22-25° C.; PMMA specimen holder ring with silicon low background holder. Prior to analysis, the samples were gently ground by means of mortar and pestle in order to obtain a fine powder. The ground sample was adjusted into a cavity of the sample holder and the surface of the sample was smoothed by means of a cover glass.

Measurement Parameters:

Scan range: 2-40 degrees 2-theta;

Scan mode: continuous;

Step size: 0.05 degrees;

Time per step: 0.5 s;

Sample spin: 30 rpm;

Sample holder: PMMA specimen holder ring with silicon low background holder.

All X-Ray Powder Diffraction peak values are calibrated with regard to standard silicon spiking in the sample.

Dynamic Vapor Sorption (DVS) Method

Make: Surface Measurement Systems

Model: DVS Advantage

Sampling Pan: Quartz Sample Pan

Procedure: About 50 mg of Sample was added to quartz sample pan. The two RH cycles (Sorption and Desorption) were performed at 25° C. In each cycle, RH was raised in 10 steps, from 0% to 95% (0, 10, 20, 30, 40, 50, 60, 70, 80 and 95%) and then back to 0% (95, 80, 70, 60, 50, 40, 30, 20, 10 and 0%). A rate of change in mass per time unit (dm/dt) of 0.002%/min was set as the equilibration parameter. At each stage, DVS hold the set parameters until the mass change reaches to 0.002%/min.

SSNMR Method:

Solid-state NMR spectra were measured at 11.7 T using a Bruker Avance III HD 500 US/WB NMR spectrometer (Karlsruhe, Germany, 2013) with 3.2 mm probehead. The $^{13}C$ CP/MAS NMR spectra employing cross-polarization were acquired using the standard pulse scheme at spinning frequency of 15 kHz and a room temperature (300 K). The recycle delay was 8 s and the cross-polarization contact time was 2 ms. The $^{13}C$ scale was referenced to α-glycine (176.03 ppm for $^{13}C$). Frictional heating of the spinning samples was offset by active cooling, and the temperature calibration was performed with $Pb(NO_3)_2$. The NMR spectrometer was completely calibrated and all experimental parameters were carefully optimized prior the investigation. Magic angle was set using KBr during standard optimization procedure and homogeneity of magnetic field was optimized using adamantane sample (resulting line-width at half-height Δν½ was less than 3.5 Hz at 250 ms of acquisition time).

TGA Method:

Thermogravimetric analysis was conducted on a TA instrument Q500 thermogravimetric analyzer. About 6.9 mg sample was placed into a tared TGA crucible and placed into a TGA furnace. The furnace was heated under nitrogen at a heating rate of 10° C./min up to 350° C.

DSC Method:

DSC was performed using a TA instrument Q2000 differential scanning calorimetry. About 2.45 mg sample was accurately weighed into an aluminum pan, covered with a lid and crimped. After crimp the aluminum lid was pin holed using needle. The sample cell was equilibrated at 20° C. and heated at a rate of 1° C./min up to 250° C. under the nitrogen atmosphere.

EXAMPLES

Preparation of Starting Materials

AT-001 can be prepared according to methods known from the literature, for example International Publication No. WO 2012/009553.

Example 1: Preparation of AT-001 Form A

AT-001 (10 grams) was transferred in 1 liter round bottom flask. 450 mL of ethanol was charged into it and was heated to temperature of about 70° C. for period of about 40 minutes to get clear solution. The obtained clear solution was filtered under vacuum at temperature of about 70° C. for period of about 15 minutes. Hot clear solution was further cooled to temperature of about 0° C. to about 5° C. at rate of 1° C./min and was maintained at temperature of about 0° C. to about 5° C. for period of about 16 hrs. The Obtained slurry was filtered under vacuum at temperature of about 25° C. to about 30° C. for the period of about 1 hour. The obtained solid was analyzed by XRPD. Form A was obtained. An XRPD pattern is shown in FIG. 1.

Example 2: Preparation of AT-001 Form A

AT-001 (0.1 grams) was dissolved in THF (1 mL) at temperature of about 60° C. The obtained clear hot solution was added into precooled (about 0° C. to about 5° C.) tertiary butyl methyl ether (10 mL) and the reaction mass was stirred at temperature of about 0° C. to about 5° C. for period of about 2 hours. The obtained slurry mass was filtered under vacuum at temperature of about 25° C. for period of about 10 minutes. The obtained solid was analyzed by XRPD. Form A was obtained.

Example 3: Preparation of AT-001 Form A

AT-001 (0.1 grams) was dissolved in 1,4-Dioxane (1 mL) at temperature of about 60° C. The obtained clear hot solution was added into precooled (about 0° C. to about 5° C.) tertiary butyl methyl ether (10 mL) and the reaction mass was stirred at temperature of about 0° C. to about 5° C. for period of about 2 hours. The obtained slurry mass was filtered under vacuum at temperature of about 25° C. for period of about 10 minutes. The obtained solid was analyzed by XRPD. Form A was obtained.

Example 4: Preparation of AT-001 Form B

AT-001 (5 grams) was dissolved in 1,4-dioxane (100 mL) at temperature of about 60° C. The clear hot solution is added into precooled (about 0° C. to about 5° C.) water (500 mL) and reaction mass was stirred at temperature of about 0° C. to about 5° C. for the period of about 2 hours. The obtained slurry mass was filtered under vacuum at temperature of about 25° C. for period of about 1 hour. The obtained solid was analyzed by XRPD. Form B was obtained. An XRPD pattern is shown in FIG. 2.

Example 5: Preparation of AT-001 Form B

AT-001 (1.5 grams) was dissolved in Formic acid (15 mL) at temperature of about 60° C. and a stock solution of AT-001 was prepared. 1 mL of clear hot stock solution was added into precooled (about 0° C. to about 5° C.) water (10 mL) and the reaction mass was stirred at temperature of about 0° C. to about 5° C. for period of about 2 hours. The obtained slurry mass was filtered under vacuum at temperature of about 25° C. for period of about for 10 minutes. The obtained solid was analyzed by XRPD. Form B was obtained.

Example 6: Preparation of AT-001 Form B

AT-001 (1.5 grams) was dissolved in Tetrahydrofuran (30 mL) at temperature of about 60° C. and a stock solution of AT-001 was prepared. 2 mL of clear hot stock solution was added into precooled (about 0° C. to about 5° C.) water (10 mL) and the reaction mass was stirred at temperature of about 0° C. to about 5° C. for period of about 2 hours. The obtained slurry mass was filtered under vacuum at 25° C. for 10 minutes. The obtained solid was analyzed by XRPD. Form B was obtained.

Example 7: Preparation of AT-001 Form B

AT-001 (Amorphous) (0.1 grams) was transferred to 5 mL test tube. 2 mL of water was added into it and obtained suspension was stirred at temperature of about 0° C. to about 5° C. for period of about 45 minutes. The obtained slurry mass was filtered under vacuum for period of about 15 minutes. The obtained solid was analyzed by XRPD. Form B was obtained.

Example 8: Preparation of AT-001 Form D

AT-001 (Amorphous) (0.05 grams) was transferred to 10 mL test tube. 0.35 mL of isopropyl acetate was added into it. The obtained suspension was shaken for 1-2 minutes and kept at temperature of about 25° C. to about 30° C. for solvent evaporation for period of about 2 days. The obtained solid was analyzed by XRPD. Form D was obtained. An XRPD pattern is shown in FIG. 3.

Example 9: Preparation of Amorphous AT-001

Figure 4:
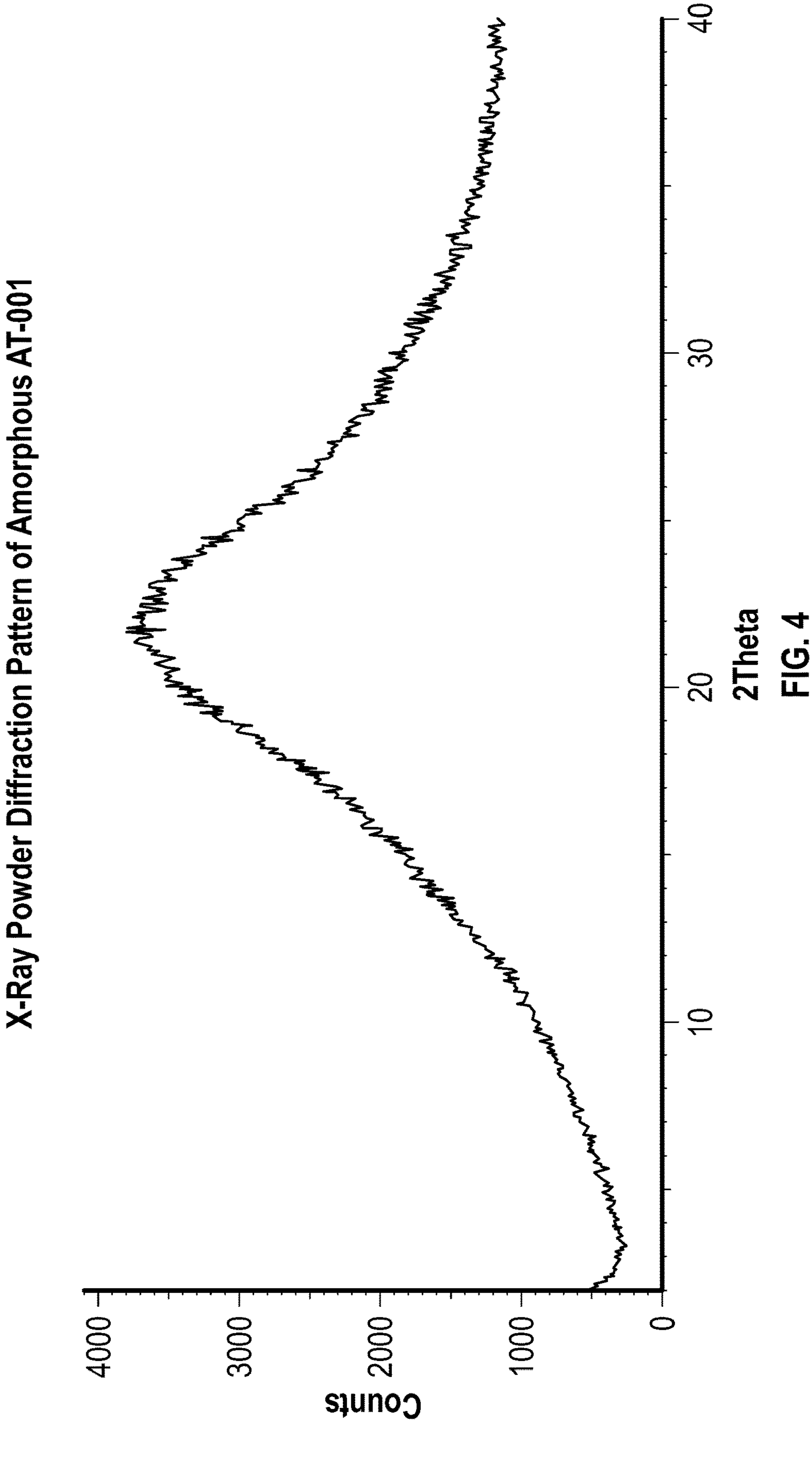
FIG. 4 shows a characteristic XRPD of amorphous AT-001.

AT-001 (10 grams) was transferred in 1 liter round bottom flask. 450 mL of ethanol was added into it and heated to temperature of about 70° C. for period of about 40 minutes to get clear solution. The Obtained clear solution was filtered under vacuum at temperature of about 70° C. for period of about 15 minutes. The Hot clear solution was cooled to temperature of about 0° C. to about 5° C. at rate of 1° C./min and was maintained at temperature of about 0° C. to about 5° C. for period of about 16 hours. The Obtained slurry was filtered under vacuum at temperature of about 25° C. to about 30° C. for period of about 1 hour. The Obtained clear mother liquor (225 mL) was subjected to distillation in a Rotary evaporator under reduced pressure (below 50 mbar) at temperature of about 60° C. for period of about 15 minutes. The Obtained solid was dried at temperature of about 60° C. on Rotary evaporator for period of about 1 hour. The obtained solid was analyzed by XRPD. Amorphous form of AT-001 was obtained. An XRPD pattern is shown in FIG. 4.

Example 10: Preparation of Amorphous AT-001

AT-001 (0.5 grams) was dissolved in 100 mL of acetone at temperature of about 50° C. in period of about 20 minutes to get clear solution. The obtained clear solution was filtered under vacuum at temperature of about 50° C. for period of about 5 minutes. The obtained clear solution was subjected to distillation at temperature of about 50° C. under reduced pressure (below 50 mbar). The obtained solid was dried at temperature of about 50° C. on Rotary evaporator for period of about 1 hour. The obtained solid was analyzed by XRPD. Amorphous form of AT-001 was obtained.

Example 11: Preparation of AT-001 Form C

AT-001 (Form B) (0.05 g) was added to quartz sample pan. The Relative Humidity ("RH") cycles Sorption (from 0% to 95% Relative Humidity) and Desorption (from 95% to 0% Relative Humidity) were carried out at temperature of about 25° C. in DVS Advantage instrument. After desorption cycle, solid was exposed to about 80% Relative Humidity at temperature of about 25° C. for period of about 1 day. The solid was analyzed by XRPD. Form C was obtained. An XRPD pattern is shown in FIG. 5.

Example 12: Preparation of AT-001 Form E

AT-001 (0.14 g) was dissolved in 10 mL of ethanol at temperature of about 70° C. for period of about 30 minutes. The obtained hot clear solution was filtered under vacuum. The clear solution was cooled to temperature of about −5° to about −10° C. and stirred at about 800 RPM for period of about 1 hour. The slurry was filtered under vacuum for period of about 15 minutes to about 20 minutes. The obtained solid was analyzed by XRPD. Form E was obtained. An XRPD pattern is shown in FIG. 6.

Example 13: Preparation of AT-001 Form F

AT-001 (Amorphous Form) (0.07 grams) was weighed and transferred in 5 mL test tube. 2 mL of Diisopropyl ether was added into it. The obtained slurry mass was stirred at temperature of about 0° C. to about 5° C. at about 400 rpm for period of about 1 day. The Slurry mass was filtered under vacuum at temperature of about 0° C. to about 5° C. for period of about 10 minutes to about 15 minutes. The obtained solid was analyzed by XRPD. Form F was obtained. An XRPD pattern is shown in FIG. 7.

Example 14: Preparation of AT-001 Form G

AT-001 (0.07 grams) was dissolved in 0.2 mL of Dimethyl Formamide at temperature of about 65° C. The obtained clear hot solution was crash cooled to temperature of about −10° C. and stirred at about 300 rpm for period of about 1 day. The obtained slurry mass was filtered under vacuum at temperature of about 0° C. to about 5° C. for period of about 10 minutes. The obtained solid was analyzed by XRPD. Form G was obtained. An XRPD pattern is shown in FIG. 8.

Example 15: Preparation of AT-001 Form H

AT-001 (0.07 grams) was dissolved in 0.2 mL of Dimethyl Acetamide at temperature of about 65° C. The obtained clear hot solution was crash cooled to temperature of about −10° C. and stirred at about 300 rpm for period of about 1 day. The obtained slurry mass was filtered under vacuum at temperature of about 0° C. to about 5° C. for period of about 10 minutes. The obtained solid was analyzed by XRPD. Form H was obtained. An XRPD pattern is shown in FIG. 9.

Example 16: Preparation of Crystalline AT-001: Nicotinamide Form AC1

AT-001 (Form A) (0.2 grams) and Nicotinamide (0.072 grams) were taken into 10 mL glass vial. 4 mL of acetonitrile was added into it. The obtained slurry was stirred at about 400 rpm at temperature of about 25° C. for period of about 1 day. The obtained solid was filtered under vacuum at temperature of about 25° C. to about 30° C., washed with 1 mL acetonitrile and kept for suction for period of about 20 minutes at same temperature. The obtained solid was analyzed by XRPD. Crystalline AT-001: Nicotinamide Form AC1 was obtained. An XRPD pattern is shown in FIG. 10.

Example 17: Preparation of Crystalline AT-001: Nicotinamide Form AC1

AT-001 (Form A) (0.1 grams) and Nicotinamide (0.029 grams) were taken into a 5 mL milling jar. 50 μL of Acetonitrile was added into it. 5 stainless steel balls were added and ball milled by using Retsch Cryomill instrument at 25 Hz frequency for about 40 minutes at temperature of about 25° C. to about 30° C. The obtained material was scratched and isolated as free solid which was analyzed by XRPD. Crystalline AT-001: Nicotinamide Form AC1 was obtained. An XRPD pattern is shown in FIG. 10.

Example 18: Preparation of Crystalline AT-001: Isonicotinamide Form AC2

AT-001 (Form A) (0.2 grams) and Isonicotinamide (0.058 grams) were taken into 5 mL test tube. 2 mL of acetonitrile was added into it. The obtained slurry was stirred at about 400 rpm at temperature of about 25° C. for period of about 1 day. The obtained solid was filtered under vacuum at temperature of about 25° C. to about 30° C. and kept for suction for period of about 15 minutes at same temperature. The obtained solid was analyzed by XRPD. Crystalline AT-001: Isonicotinamide Form AC2 was obtained. An XRPD pattern is shown in FIG. 11.

Example 19: Preparation of Crystalline AT-001: Nicotinamide Form AC3

AT-001 (Form A) (0.2 grams) and Nicotinamide (0.087 grams) were taken into 10 mL glass vial. 4 mL of acetonitrile was added into it. The obtained slurry was stirred at about 400 rpm at temperature of about 25° C. for period of about 1 day. The obtained solid was filtered under vacuum at 25° C. to about 30° C., washed with ImL acetonitrile and kept for suction for period of about 20 minutes at same temperature. Further, the solid was dried under vacuum in Vacuum Tray Dryer at temperature of about 80° C. for period of about 2 hours. The obtained solid was analyzed by XRPD. Crystalline AT-001: Nicotinamide Form AC3 was obtained. An XRPD pattern is shown in FIG. 12.

Example 20: Preparation of AT-001 Form I

AT-001 (Form A) 0.5 grams was taken into 20 mL test tube and 5 mL of N-methyl Formamide was added into it. The obtained suspension was stirred at temperature of about 60° C. for the period of about 19 hours. The obtained slurry mass was filtered under vacuum at temperature of about 60° C. and kept on suction for drying for period of about 2 hours. The solid was further dried at temperature of about 45° C. in air tray drier for period of about 2 hours. The obtained solid was further slurried in 4 mL of MTBE at 25° C. for period of about 15 minutes. The obtained slurry mass was filtered under vacuum for period of about 15 minutes. The obtained solid was analyzed by XRPD. Form I was obtained. An XRPD pattern is shown in FIG. 13.

Example 21: Preparation of AT-001 Form I

AT-001 (0.07 grams) was dissolved in 1.2 mL of N-methyl Formamide at temperature of about 65° C. The obtained clear hot solution was crash cooled to −10° C. and stirred at 300 rpm at −10° C. for period of about 1 day. The obtained slurry mass was filtered under vacuum at temperature of about 0° C. to about 5° C. for period of about 10 minutes. The obtained solid was analyzed by XRPD. Form I was obtained.

Example 22: Preparation of AT-001 Form I

AT-001 (Amorphous) (0.07 grams) was taken in a 15 mL test tube. ImL N-Methyl Formamide was added into it. The reaction mixture was run through temperature cycling program from temperature of about 0° C. to about 70° C. at the rate of 0.2° C./min; hold at temperature of about 70° C. for period of about 1 hour and 70° C. to 0° C. at the rate of 0.2° C./min; hold at temperature of about 0° C. for period of about 1 hour. The heat-cool cycle was repeated thrice. After heat-cool cycle, the reaction mass was filtered under vacuum for period of about 10 minutes. The obtained solid was analyzed by XRPD. Form I was obtained.

Example 23: Preparation of AT-001 Form J

AT-001 (0.5 grams) was taken in a 20 mL test tube. 14 mL Formamide was added into it. The reaction mixture was stirred at temperature of about 70° C. for period of about 30 minutes. Clear hot solution was cooled to temperature of about −10° C. at the rate of 0.2° C./min and maintained at temperature of about −10° C. for period of about 11 hours. The obtained slurry mass was filtered under vacuum at temperature of about 0° C. to about 5° C. and kept on suction for drying for period of about 2 hours. The obtained solid was analyzed by XRPD. Form J was obtained. An XRPD pattern is shown in FIG. 14.

Example 24: Preparation of AT-001 Form J

AT-001 (0.05 grams) was dissolved in 1.4 mL of Formamide at temperature of about 60° C. The obtained clear hot solution was slowly cooled to temperature of about 0° C. at the rate 0.5° C./min and stirred at 400 rpm at temperature of about 0° C. for period of about 1 day. The obtained slurry mass was filtered under vacuum at temperature of about 0° C. to about 5° C. for period of about 5 minutes to about 10 minutes. The obtained solid was analyzed by XRPD. Form J was obtained.

Example 25: Preparation of AT-001 Form J

AT-001 (Form A) (0.5 grams) was taken in a 20 mL test tube. 14 mL Formamide was added into it. The reaction mixture was stirred at temperature of about 0° C. to about 5° C. for period of about 19 hours. The obtained slurry mass was filtered under vacuum at temperature of about 0° C. to about 5° C. and kept on suction for drying for period of about 2 hours. The obtained solid was further slurried in 4 mL of MTBE at temperature of about 25° C. for period of about 20 minutes. The obtained slurry mass was filtered under vacuum for period of about 15 minutes. The obtained solid was analyzed by XRPD. Form J was obtained.

Example 26: Preparation of AT-001 Form J

AT-001 (0.07 grams) was dissolved in 2.0 mL of Formamide at temperature of about 65° C. The obtained clear hot solution was crash cooled to temperature of about −10° C. and stirred at about 300 rpm at temperature of about −10° C. for period of about 1 day. The obtained slurry mass was filtered under vacuum at temperature of about 0° C. to about 5° C. for period of about 10 minutes. The obtained solid was analyzed by XRPD. Form J was obtained.

Example 27: Preparation of AT-001 Form K

AT-001 (Amorphous Form) 0.07 grams was weighed and transferred in 5 mL test tube. 2 mL of Formamide was added into it at temperature of about 25° C. The obtained slurry mass was stirred at temperature of about 0° C. to about 5° C. at 400 rpm for period of about 1 day. Slurry mass was filtered under vacuum at temperature of about 0° C. to about 5° C., washed with 2 mL of MTBE and kept on suction at temperature of about 25 to about 30° C. for period of about 10 minutes to about 15 minutes. The obtained solid was analyzed by XRPD. Form K was obtained. An XRPD pattern is shown in FIG. 15.

The invention claimed is:

1. A composition comprising a crystalline Form B of 2-(8-oxo-7-((5-(trifluoromethyl)benzo[d]thiazol-2-yl)methyl)-7,8-dihydropyrazino[2,3-d]pyridazin-5-yl)acetic acid characterized by data selected from one or more of the following:

a) an XRPD pattern having peaks at 7.5, 16.6, 17.1, 27.9 and 31.1 degrees 2-theta±0.2 degrees 2-theta;

b) a solid state $^{13}C$ NMR spectrum having peaks at 36.6, 57.3, 118.7, 145, 148.8 and 168.3 ppm±0.2 ppm;

c) combinations of a) and b).

2. The composition according to claim 1, wherein the crystalline Form B of 2-(8-oxo-7-((5-(trifluoromethyl)benzo[d]thiazol-2-yl)methyl)-7,8-dihydropyrazino[2,3-d]pyridazin-5-yl)acetic acid is a hydrate.

3. The composition according to claim 1, which contains no more than about 20% of any other crystalline forms of 2-(8-oxo-7-((5-(trifluoromethyl)benzo[d]thiazol-2-yl)methyl)-7,8-dihydropyrazino[2,3-d]pyridazin-5-yl)acetic acid.

4. The composition according to claim 1, which contains no more than about 20% of amorphous 2-(8-oxo-7-((5-(trifluoromethyl)benzo[d]thiazol-2-yl)methyl)-7,8-dihydropyrazino[2,3-d]pyridazin-5-yl)acetic acid.

5. A pharmaceutical formulation comprising the composition according to claim 1 with at least one pharmaceutically acceptable excipient.

6. A medicament comprising the composition according to claim 1.

* * * * *